(12) United States Patent
Brasfield

(10) Patent No.: US 9,835,602 B2
(45) Date of Patent: *Dec. 5, 2017

(54) TARGET ODOR DETECTION AND SECURITY METHOD

(71) Applicant: Freddie R. Brasfield, Oak Ridge, TN (US)

(72) Inventor: Freddie R. Brasfield, Oak Ridge, TN (US)

( * ) Notice: Subject to any disclaimer, the term of this patent is extended or adjusted under 35 U.S.C. 154(b) by 579 days.

This patent is subject to a terminal disclaimer.

(21) Appl. No.: 14/326,852

(22) Filed: Jul. 9, 2014

(65) Prior Publication Data

US 2014/0311219 A1    Oct. 23, 2014

Related U.S. Application Data

(63) Continuation of application No. 13/281,298, filed on Oct. 25, 2011, now Pat. No. 8,806,914, which is a continuation-in-part of application No. 13/160,075, filed on Jun. 14, 2011, now Pat. No. 8,701,463, which is a continuation-in-part of application No. 13/029,839, filed on Feb. 17, 2011, now Pat. No. 8,671,737, which is a continuation-in-part of application No. 11/859,851, filed on Sep. 24, 2007, now Pat. No. 7,913,540.

(51) Int. Cl.
| | |
|---|---|
| *G01N 33/00* | (2006.01) |
| *G01N 1/24* | (2006.01) |
| *G07C 9/00* | (2006.01) |
| *G07C 9/02* | (2006.01) |
| *G01N 1/02* | (2006.01) |

(52) U.S. Cl.
CPC .......... *G01N 33/0001* (2013.01); *G01N 1/24* (2013.01); *G01N 33/0004* (2013.01); *G01N 33/0057* (2013.01); *G07C 9/00126* (2013.01); *G07C 9/02* (2013.01); *G01N 2001/022* (2013.01)

(58) Field of Classification Search
CPC .......... G01N 33/0001; G01N 33/0057; G01N 33/0004; G01N 2001/022; G07C 9/02
See application file for complete search history.

(56) References Cited

U.S. PATENT DOCUMENTS

| | | |
|---|---|---|
| 3,357,257 A | 12/1967 | Herndon et al. |
| 3,883,739 A | 5/1975 | Jenkins |
| 4,022,054 A | 5/1977 | Biederman |
| 4,063,519 A | 12/1977 | Pretini |

(Continued)

FOREIGN PATENT DOCUMENTS

| | | |
|---|---|---|
| GB | 2440937 | 2/2008 |
| WO | 2002/29744 | 4/2002 |

(Continued)

OTHER PUBLICATIONS

EPO Office Action, Communication pursuant to Article 94(3) EPC, Application No. 12 747 834.5-1559, dated Apr. 19, 2017.

(Continued)

*Primary Examiner* — John Fitzgerald
(74) *Attorney, Agent, or Firm* — Robinson IP Law, PLLC

(57) ABSTRACT

A target odor detecting method for screening odor emitters in a relatively confined space using an animate and/or inanimate odor detector to detect one or more target odors.

7 Claims, 21 Drawing Sheets

(56) References Cited

U.S. PATENT DOCUMENTS

| | | | |
|---|---|---|---|
| 4,197,675 A * | 4/1980 | Kelly | E05F 15/72 340/634 |
| 4,202,200 A | 5/1980 | Ellson | |
| 4,411,156 A | 10/1983 | Lowe | |
| 4,586,441 A | 5/1986 | Zekich | |
| 4,896,547 A | 1/1990 | Amey et al. | |
| 4,987,767 A | 1/1991 | Corrigan et al. | |
| 5,109,691 A | 5/1992 | Corrigan et al. | |
| 5,600,303 A | 2/1997 | Husseiny et al. | |
| 5,711,111 A | 1/1998 | Nyffenegger et al. | |
| 5,753,832 A | 5/1998 | Bromberg et al. | |
| 5,878,529 A | 3/1999 | Huber | |
| 5,915,268 A | 6/1999 | Linker et al. | |
| 6,018,984 A | 2/2000 | McGinley et al. | |
| 6,073,499 A | 6/2000 | Settles | |
| 6,295,860 B1 | 10/2001 | Sakairi et al. | |
| 6,334,365 B1 | 1/2002 | Linker et al. | |
| 6,366,203 B1 | 4/2002 | Burns | |
| 6,374,662 B1 | 4/2002 | Oda et al. | |
| 6,375,697 B2 | 4/2002 | Davies | |
| 6,558,626 B1 | 5/2003 | Aker et al. | |
| 6,610,977 B2 | 8/2003 | Megerle | |
| 6,655,302 B1 * | 12/2003 | Ross | G07F 19/205 109/10 |
| 6,708,572 B2 | 3/2004 | Jenkins et al. | |
| 6,735,274 B1 | 5/2004 | Zahavi et al. | |
| 6,782,845 B1 | 8/2004 | Schmidt et al. | |
| 6,790,249 B2 | 9/2004 | Davies | |
| 6,823,714 B2 | 11/2004 | Megerle | |
| 6,919,202 B2 | 7/2005 | Lewis et al. | |
| 6,972,693 B2 | 12/2005 | Brown et al. | |
| 7,023,339 B2 | 4/2006 | Stomski | |
| 7,091,856 B2 | 8/2006 | Tibi et al. | |
| 7,141,786 B2 | 11/2006 | McGann et al. | |
| 7,180,441 B2 | 2/2007 | Rowe et al. | |
| 7,188,513 B2 | 3/2007 | Wilson | |
| 7,357,043 B2 | 4/2008 | Cumming et al. | |
| 7,401,438 B2 | 7/2008 | Wild | |
| 7,717,066 B2 | 5/2010 | Drolet | |
| 7,765,072 B2 * | 7/2010 | Eiler | F24F 3/16 702/31 |
| 7,913,540 B2 | 3/2011 | Brasfield | |
| 8,671,737 B2 * | 3/2014 | Brasfield | G01N 33/0001 73/23.34 |
| 8,701,463 B2 * | 4/2014 | Brasfield | G01N 33/0001 73/23.34 |
| 8,806,914 B2 * | 8/2014 | Brasfield | G01N 33/0004 73/23.34 |
| 2001/0049926 A1 | 12/2001 | Davies | |
| 2003/0071590 A1 * | 4/2003 | Roman | E05F 15/70 318/282 |
| 2003/0085348 A1 | 5/2003 | Megerle | |
| 2004/0232054 A1 | 11/2004 | Brown et al. | |
| 2005/0009444 A1 | 1/2005 | Davis et al. | |
| 2006/0061450 A1 | 3/2006 | Tibi et al. | |
| 2006/0150872 A1 | 7/2006 | Mesinger | |
| 2006/0226998 A1 | 10/2006 | Wilson | |
| 2007/0056392 A1 | 3/2007 | Cumming et al. | |
| 2009/0038555 A1 | 2/2009 | Reese | |
| 2009/0077908 A1 | 2/2009 | Brasfield | |
| 2009/0139459 A1 | 6/2009 | Habacivch et al. | |
| 2009/0162196 A1 | 6/2009 | Drolet | |
| 2010/0180667 A1 | 7/2010 | Bender et al. | |
| 2012/0103060 A1 | 5/2012 | Brasfield | |
| 2012/0131985 A1 | 5/2012 | Brasfield | |
| 2012/0151993 A1 | 6/2012 | Brasfield | |

FOREIGN PATENT DOCUMENTS

| | | |
|---|---|---|
| WO | 2004/085251 | 10/2004 |
| WO | 2006/085999 | 8/2006 |
| WO | WO2006/085999 | 8/2006 |

OTHER PUBLICATIONS

EPO Office Action, Communication pursuant to Article 94(3) EPC, Application No. 12 800 830.7-1559, dated Apr. 19, 2017.
Office Action dated Jul. 19, 2017, Israeli Patent Office, Israel Patent Application No. 227980.

* cited by examiner

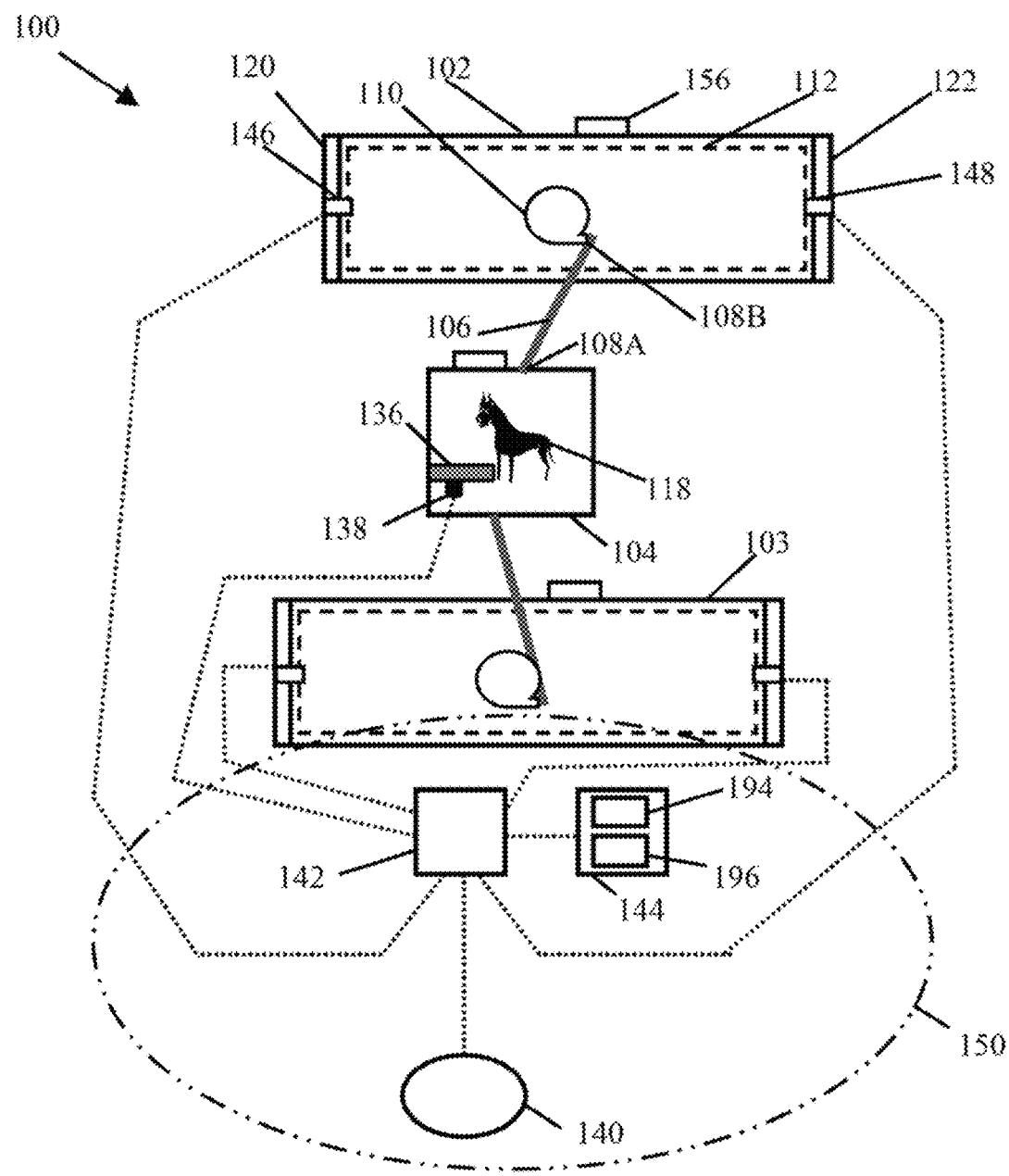

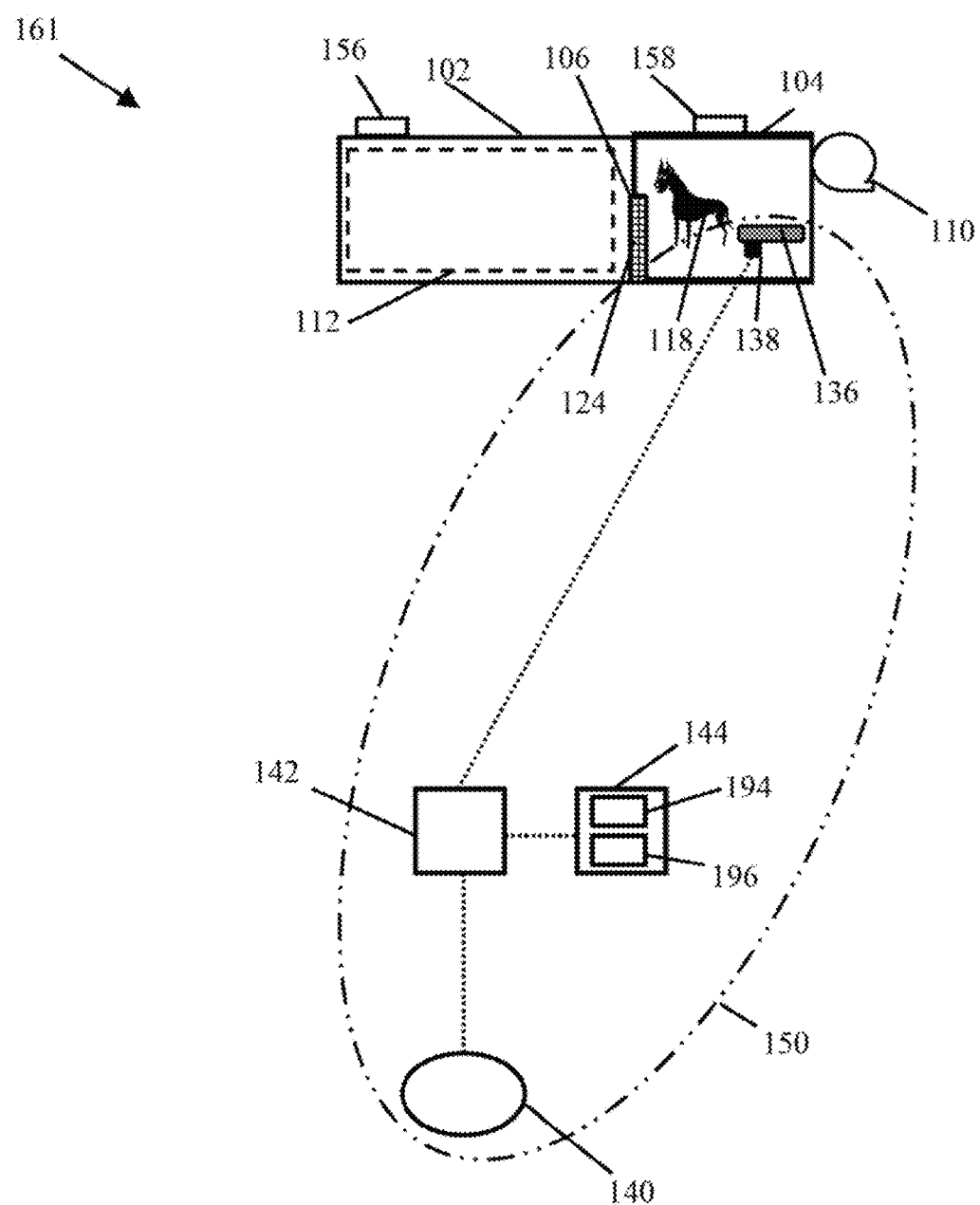

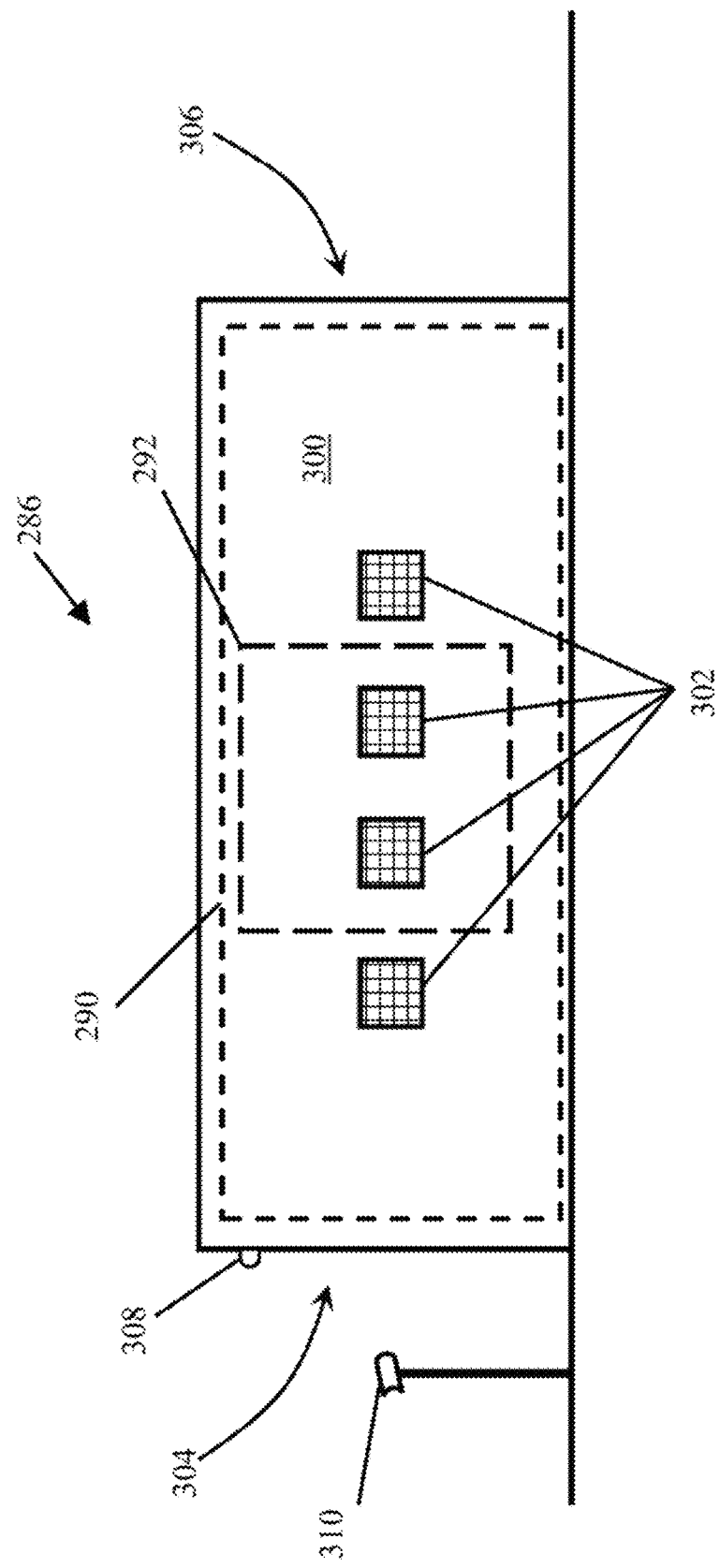

TARGET ODOR DETECTION AND SECURITY METHOD

CROSS-REFERENCE(S) TO RELATED APPLICATION(S)

This application claims priority as a continuation application of pending U.S. application Ser. No. 13/281,298 to Freddie R. Brasfield entitled "Target Odor Detection and Security Apparatus" which was originally filed on Oct. 25, 2011, which is a continuation-in-part of U.S. application Ser. No. 13/160,075 (now U.S. Pat. No. 8,701,463) to Freddie R. Brasfield entitled "Target Odor Detection and Security Apparatus" which was originally filed on Jun. 14, 2011, which is a continuation-in-part of U.S. application Ser. No. 13/029,839 (now U.S. Pat. No. 8,671,737) to Freddie R. Brasfield entitled "Target Odor Detection and Security Apparatus" which was originally filed on Feb. 17, 2011, which claims priority to and is a continuation-in-part of U.S. application Ser. No. 11/859,851 (now U.S. Pat. No. 7,913,540) to Freddie R. Brasfield entitled "Odor Screening System," the contents of which are incorporated herein by reference in their respective entireties.

FIELD

This disclosure relates to the field of odor screening for distinctive odors emitted by prohibited materials. More particularly, this disclosure relates to a method and apparatus for collecting odor samples from and/or vehicles and supplying the odor samples to an animate and/or inanimate odor detector for identification of target odors of prohibited materials.

BACKGROUND

There are many situations in which pedestrians may be carrying materials which are prohibited from transport into or out of a designated area. Some examples are airports, sporting arenas and high security facilities. The prohibited materials may include, for example, explosives, drugs or even a product being stolen.

One method for screening for various materials is to individually search each pedestrian for the prohibited material. Unfortunately, individual searching is extremely time-consuming and requires an inordinate number of searchers and an inordinate period of time.

It is known that many prohibited materials such as explosives and drugs emit odors which are distinctive and can be detected in very small quantities by dogs, other animals, and/or specialized inanimate detectors which have been trained or otherwise calibrated to identify such target odors. However, bringing certain animals into direct contact with a large number of pedestrians presents difficulties. Some people are fearful of certain animals and a person being screened may cause harm to a highly trained dog or its handler. Similarly, bringing expensive and often cumbersome detection equipment into direct contact with a large number of pedestrians and/or vehicles presents risks. Discrete placement of such equipment is important as well as the protection of the equipment itself, which is often expensive, and protection of personnel responsible for such equipment.

What is needed, therefore, is a reliable, consistent, and rapid system to screen persons or conveyances and obtain consistent positive identifications of prohibited material while minimizing false-positive identifications of prohibitive material.

SUMMARY

The above and other needs are met by a method for screening an odor emitter, the method comprising the steps of providing access to an entry point to a security zone for an odor emitter wherein the entry point comprises a rotatable door through which an odor emitter must pass through prior to entering the security zone, wherein the rotatable door includes an enclosed portion defining a screening zone, the enclosed portion including a plurality of adjacent rotatable panes, a curved wall fixed relative to the plurality of rotatable panes, a base member, and a ceiling member; moving air through the screening zone wherein at least some of the moved air is directed to an observation room; screening the air from the screening zone that has been moved to the observation room; and determining whether a target odor is present in the moved air present in the observation room. In one example, the step of screening includes screening such air using an animate odor detector. In another example, the step of screening includes screening such air using an inanimate odor detector. In yet another example, the step of screening includes screening such air using both at least an animate odor detector and an inanimate odor detector.

In a related example, the screening method further comprises the step of determining the type of target odor present if a target odor is detected in the moved air present in the observation room.

In yet another related example, the screening method further comprises the step of locking down the rotatable door so that the odor emitter being screened is trapped between the adjacent rotatable panes and the curved wall. Alternatively, the method further comprises the step repulsing the odor emitter away from the security zone.

In a related example, the method further comprises the step of closing any vents, doors, or other openings to the screening zone, thereby sealing the screening zone so that any potential airborne threat cannot be spread any further from the screening zone to adjacent areas.

In another version, a method for screening an odor emitter comprises the steps of providing access to an ingress portal to a screening station of a security apparatus for screening an odor emitter, wherein the security apparatus comprises the screening station, an observation room situated remote from the screening station, a conduit between the screening station and the observation room, and an airflow inducer; and wherein the screening station further comprises an enclosure, an ingress portal providing access to the enclosure, an associated ingress lockable door, an egress portal providing access to a security zone, and an associated egress lockable door; moving air through the screening zone using the airflow inducer wherein at least some of the moved air is directed to the observation room; screening the air from the screening zone that has been moved to the observation room; and determining whether a target odor is present in the moved air present in the observation room. In one example, the step of screening includes screening such air using an animate odor detector. In another example, the step of screening includes screening such air using an inanimate odor detector. In yet another example, the step of screening includes screening such air using both at least an animate odor detector and an inanimate odor detector.

In one related example, the screening method further comprises the step of determining the type of target odor present if a target odor is detected in the moved air present in the observation room.

In a related example, the screening method further comprises the step of closing and locking the ingress lockable door and the egress lockable door so that the odor emitter being screened is trapped between the ingress lockable door and the egress lockable door.

The screening method may further comprise the steps of releasing odor emitter away from the screening station or, alternatively, closing and locking the egress lockable door and repulsing the odor emitter from the screening station.

In a related example, the screening method further comprises the step of closing any vents, doors, or other openings to the screening zone, thereby sealing the screening zone so that any potential airborne threat cannot be spread any further from the screening zone to adjacent areas.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

FIG. 4B shows a somewhat schematic side view of the target odor detection apparatus shown in FIG. 4A;

FIG. 5 shows a somewhat schematic end view of a target odor detection apparatus;

FIG. 10 shows a somewhat schematic side view of a target odor detection apparatus;

DETAILED DESCRIPTION

Figure 1:
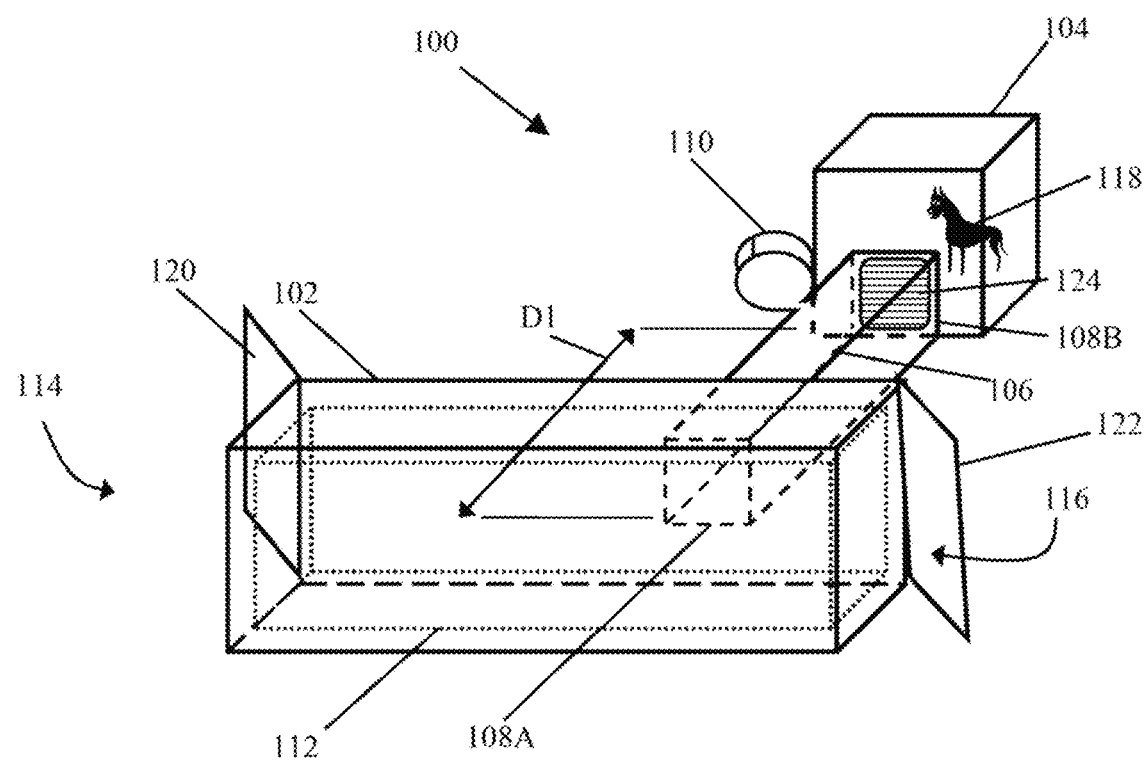
FIG. 1 shows a somewhat schematic perspective view of a target odor detection apparatus.

Various terms used herein are intended to have particular meanings Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Air: broadly defined to include a scientific definition of "air" and/or other pure gases and gas mixtures and all solid, liquid, and gaseous substances entrained therein.

Airflow inducer: an apparatus used to cause air to move relative to the apparatus (e.g., a fan, a pump, or other similar device, with or without moving mechanical parts) by pushing or pulling such air.

Animate Odor Detector: An animal that has been trained or otherwise has learned a specific behavioral response (or "trained signal") when such animal detects a specific target odor. Animate odor detectors can include, for example, canines, mice, monkeys, and other animals capable of detecting a target odor(s) at very low concentrations and exhibiting learned or trained behavior based on the detection of such target odors(s).

Inanimate Odor Detector: A non-living device that has been calibrated or otherwise has learned through, for example, computer-based learning algorithms and/or programs, how to properly detect and identify a specific target odor. Inanimate odor detectors can include, for example, products available from Scent Detection Technologies, Ltd. of Herzliya Pituach, Israel, and ScentLogix of Annapolis, Md., including such technologies as ion mobility spectrometry, gas chromatography, mass spectrometry, and liquid chromatography, many or all of which individually or in combination are capable of detecting a target odor(s) at very low concentrations.

Conduit: an apparatus configured to direct or otherwise channel gas from a first location to a second location.

Engagement Apparatus: an apparatus to be acted upon (i.e., "engaged") directly or indirectly by an animate odor detector.

Gas: broadly defined to include pure gases and gas mixtures (including solid and liquid particles entrained therein).

Porous structure: a structure including a plurality of apertures there through for allowing gas to migrate or otherwise be propelled from a first side of the structure to an opposed side of the structure.

Security Screening Session: A period of time during which one or more odor emitters are being screened for a target odor.

Target Odor: an odor of interest that may indicate the presence of a contraband substance such as, for example, illegal narcotics, explosives, chemical weapons, biological weapons, or anything deemed a potential threat to an area being secured.

Trained signal: a specific trained or learned behavioral response given by an animate odor detector in response to the animate odor detector detecting a target odor.

Triggering event: a situation in which an animate odor detector gives a trained signal, indicating that a target odor has been detected.

Wall: an object situated in any orientation, having a length much greater than its thickness, and presenting a substantially continuous surface except apertures or other objects are encountered there through or thereon.

FIG. 1 shows an embodiment of a security apparatus 100 including a screening station 102, an observation room 104 situated remote from the screening station 102, a conduit 106 including a first end 108A and a second end 108B, and an airflow inducer 110. The screening station 102 includes a three dimensional screening zone 112 where persons, animals, and/or things (collectively, "odor emitters") pass through in order to be screened for one or more target odors. The screening zone 112 can be configured as a hallway through which multiple persons (up to about 100) can pass at one time at varying rates of speed and location within the hallway depending on the degree of security desired for the particular situation. The screening zone 112 is defined adjacent an ingress portal 114 through which odor emitters enter the screening station 102, and an egress portal 116 through which odor emitters exit the screening station 102. The conduit 106 can be configured to have various possible configurations, but preferably is configured such that the observation room 104 is a distance D1 from about 50 feet to about 250 ft, and most preferably from about 175 ft to about 225 ft, from the screening zone 112. The screening station 102 is attached adjacent the conduit 106 proximate the first end 108A of the conduit 106 and the observation room 104 is attached adjacent the conduit 106 proximate the second end 108B of the conduit. The air inducer 110 is used to push, pull, or otherwise induce gas flow from within the screening zone 112, through the conduit 106 to the observation room 104, taking odors from odor emitters being screened with it so that an animate odor detector 118 located in the observation room 104 is exposed to such odors to screen the odors for one or more target odors. As an example, when a dog having an average weight of from about 15 to about 70 pounds is used as an animate odor detector, a preferred flow rate of air past the dog ranges from about 1500 cubic feet per minute (cfm) to about 2500 cfm. The cross-sectional area through which air is flowing preferably ranges from about 5 $ft^2$ to about 10 $ft^2$. Smaller animals as animate odor detectors preferably are exposed to a smaller volumetric flow rate of air roughly proportional to the weight of the particular animate odor detector(s) being used.

Although an animate odor detector 118 is used in this and other examples, other embodiments may include one or more inanimate odor detectors. The various figures shown herein with representations showing animate odor detectors are contemplated to alternatively or additionally include inanimate odor detectors.

If the animate odor detector 118 senses the presence of target odor for which it has been trained, it will respond with a trained signal to alert a handler that a specific odor has been identified. The animate odor detector 118 is rewarded and the handler, or other security officers, may then direct the interception, detention, or release of the odor emitter or group of odor emitters who emitted the detected target odor. Detaining within the screening station 102 an odor emitter that causes a triggering event may be desirable or undesirable depending on numerous factors including what type of target odor was identified, whether the screening station 102 is fortified or otherwise resistant to explosive blasts and/or small projectiles, and whether the screening station 102 is substantially airtight. For example, if an odor emitter emits a target odor resulting in a triggering event from an animate odor detector trained for high explosives, it may be desirable to lock down the screening station 102 and detain the odor emitter inside if the screening station 102 is reinforced for explosives. If, however, the screening station 102 is not reinforced or otherwise resistant to high explosives, it may be more desirable to temporarily release the odor emitter in a direction away from a protected building or event. If a target odor indicating narcotics caused a triggering event, however, it may be more desirable to detain the odor emitter regardless of whether the screening station 102 is reinforced because there is no imminent threat of an explosion. Similar logical scenarios are contemplated regarding firearms, chemical weapons, and biological weapons, and the protocol used in these situations would vary based on the embodiment of the security apparatus 100 that is used.

Figure 2A:
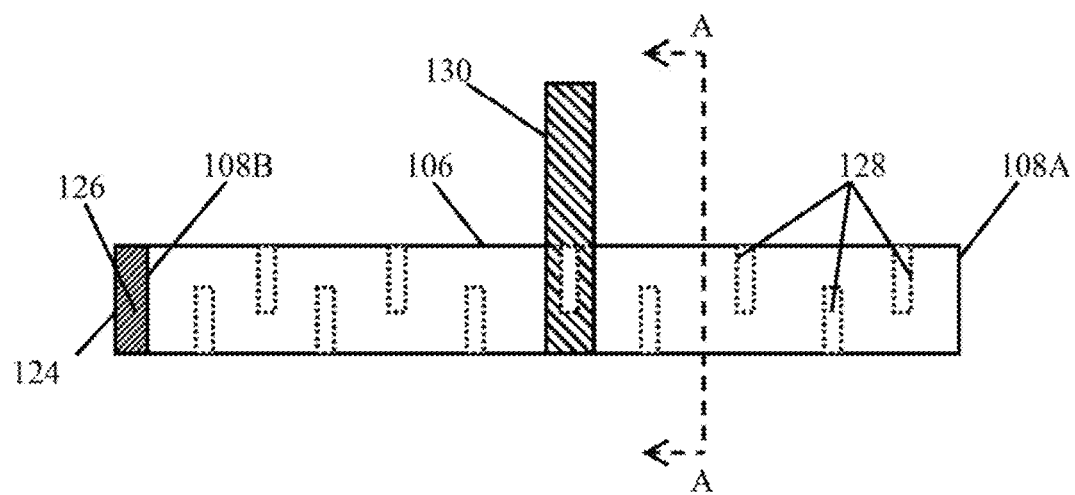
FIG. 2A shows a somewhat schematic side view of a conduit and some security features associated therewith.
Figure 2B:
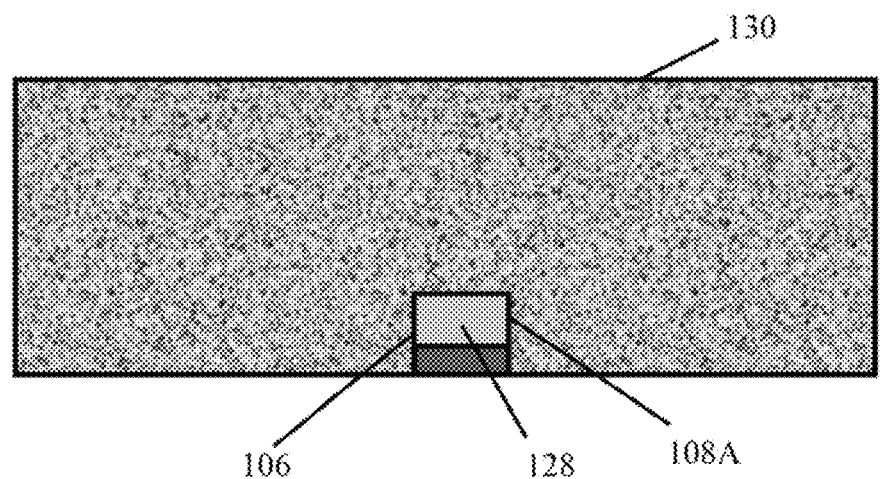
FIG. 2B shows a view cut along line A-A from FIG. 2A.

Preferably, the security apparatus 100 includes a first door 120 for closing the ingress portal 114 and a second door 122 for closing the egress portal 116. Also, the security structure preferably includes a porous structure 124 defining a porous zone 126 between the screening zone 112 and the conduit 106. The porous structure 124 can come in many forms and can be used, for example, to filter air flowing through the porous zone 126, to block an odor emitter from entering the conduit 106, and to act as a visual barrier to prevent an odor emitter from seeing down the conduit. In addition to or in the alternative to use of the porous structure 124, as shown in FIGS. 2A-2B, the conduit 106 can include one or more baffles 128 for protecting the animate odor detector 118 and anyone else in the observation room 104 from, for example, explosive debris, small arms fire, chemical weapons use, and/or biological weapons use emanating from or near the screening zone 112. In addition to baffles 128 within the conduit 106, one or more protective walls 130 are included in some embodiments to further isolate the observation room 104 from the screening zone 112.

Figure 3:
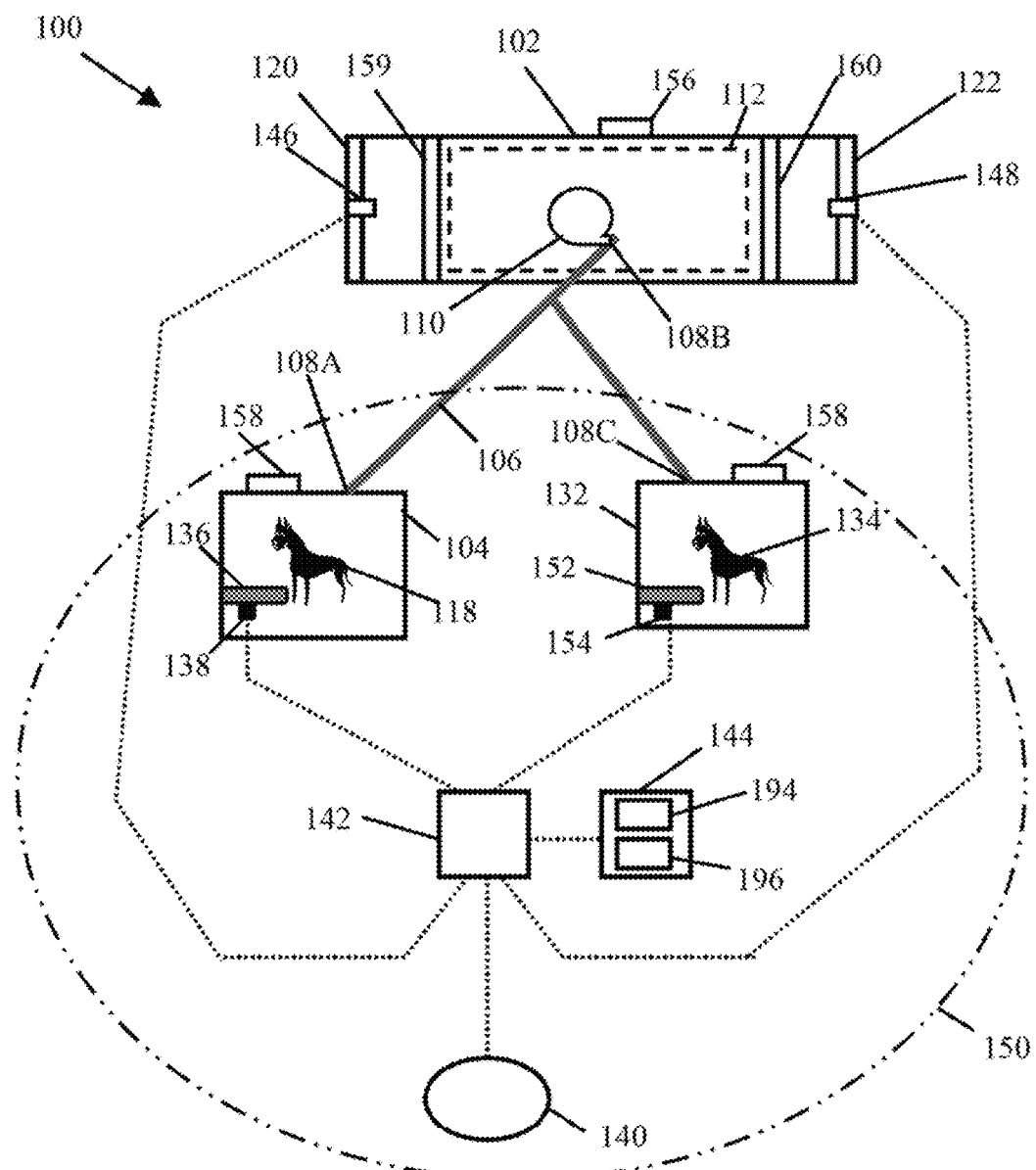
FIG. 3 shows a somewhat schematic side view of a target odor detection apparatus.

In some embodiments as illustrated, for example, in FIG. 3, the security apparatus 100 includes a second observation room 132 remote from the screening zone 112, wherein the conduit 106 further includes a third end 108C attached adjacent the second observation room 132. Preferably, a second animate odor detector 134 trained to detect one or more target odors is placed in the second observation room 132 to screen odor emitters as they pass through the screening zone. Preferably, the second animate odor detector 134 is tasked with screening for a different target odor than the first animate odor detector 118 is screening for. In some embodiments, the observation room 104 includes an engagement apparatus 136 (e.g., a scratch pad, a lever, a touchscreen, a light beam) including a sensing device 138 attached adjacent thereto. As shown in FIG. 3, the sensing device 138 is in communication with an event indicator 140 and a computational device 142, which further includes an internal or external memory unit 144. The computational device 142 can include, for example, personal computers, laptop computers, integrated circuits (simple or complex such as, for example, an application-specific integrated circuit (ASIC)), embedded computers, servers, control processing units (CPUs), microprocessors. Data corresponding to a minimum threshold of input on the engagement apparatus 136 (e.g., a minimum pressure value, a minimum amount of light interruption, a minimum vibration value) is saved, uploaded, downloaded, or otherwise provided to the memory unit 144. During operation of the security apparatus 100, the engagement apparatus 136 is substantially continuously monitored by the computational device 142 so that the event indicator 140 is activated if/when an animate odor detector engages the engagement apparatus 136 with at least a minimum threshold of input force and/or activity. The sensing device 138 can include, for example, a microswitch, a vibration sensor, an accelerometer, a touchpad (e.g., piezoelectric), one or more light detectors, a motion detector, and/or other related sensor technology known to person having ordinary skill in the art.

Figure 4A:
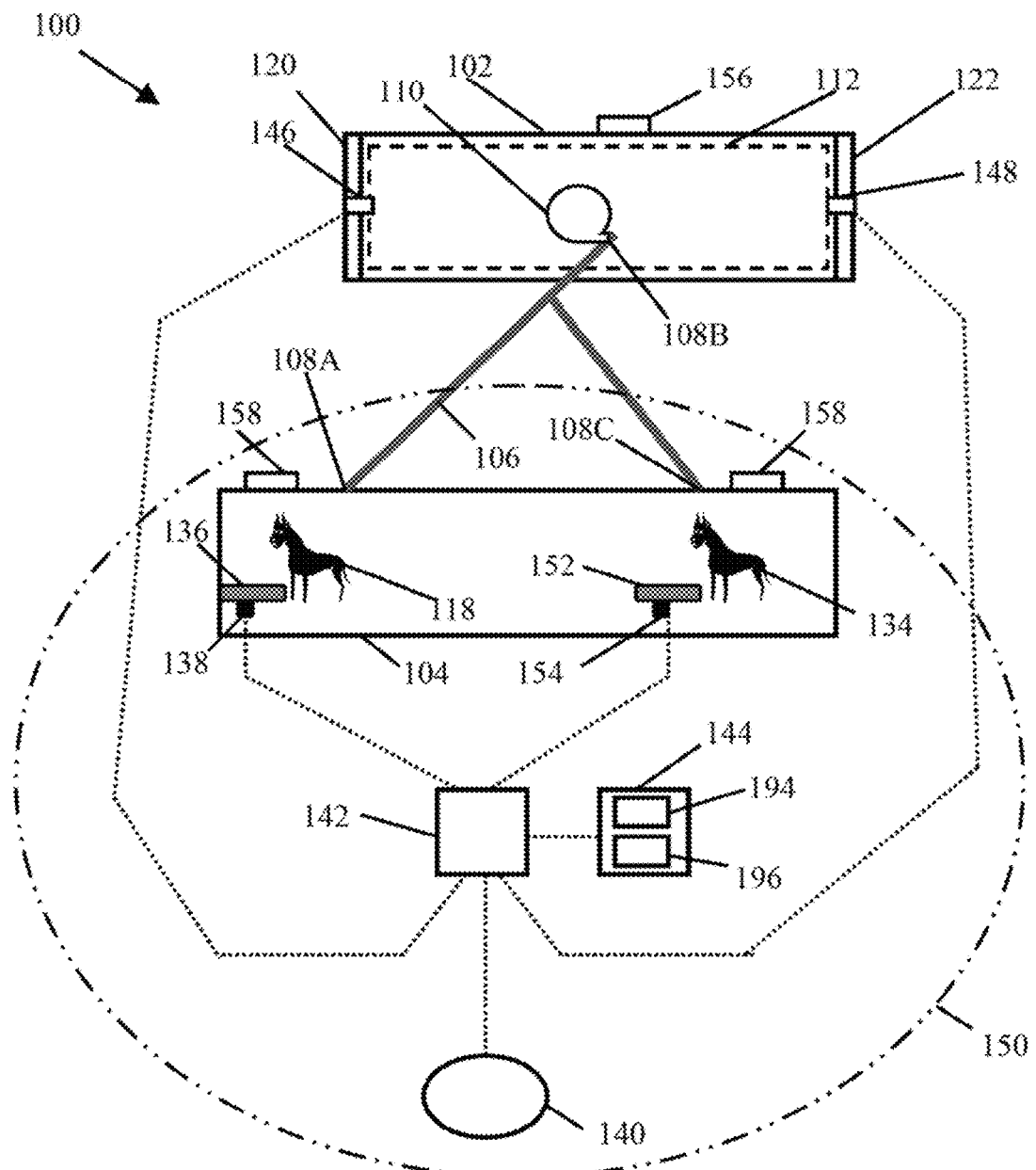
FIG. 4A shows a somewhat schematic side view of a target odor detection apparatus.

The event indicator 140 can come in many different forms including, for example, a siren, a flashing light, and/or one or more security assets that can be activated in response to a triggering event. In one example, the security apparatus 100 includes a first lock 146 (e.g., an automated and/or manual bolt lock or magnetic lock), a second lock 148, and a control system 150 which can include, for example, the sensing device 138, the event indicator 140, the computational device 142, and the memory unit 144. The first door 120 is engageable with the first lock 146 and the second door is engageable with the second lock 148, and the lock status of one or all doors is/are preferably monitored and partially or completely controlled by the control system 150. In one embodiment wherein at least two separate animate odor detectors are used to screen odor emitters, the resultant control response based on a triggering event initiated by, for example, the first animate odor detector 118 is different from the resultant control response based on a triggering event initiated by the second animate odor detector 134. As shown in FIG. 4A, the first animate odor detector 118 and the second animate odor detector 134 can be in the same observation room 104 with the first animate odor detector assigned to the first engagement apparatus 136 and the second animate odor detector 134 assigned to a second engagement apparatus 152 and second sensing device 154. Regardless of how the animate odor detectors are situated, the first engagement apparatus 136 can be associated with a first type of triggering event (e.g., explosive material), whereas the second engagement apparatus 152 is associated with a second type of triggering event (e.g., illegal narcotics). The control response to the first triggering event can, for example, be to activate, close, and lock the first door 120 and the second door 122, whereas the control response to the first triggering event can, for example, be to activate, close, and lock only one of the doors, activate a siren and/or flashing light, or do nothing. In a related embodiment shown in FIG. 4B, a single animate odor detector 118 can be used to screen a plurality of screening stations including, for example, the screening station 102 shown in FIG. 4A and a second screening station 103.

Preferably, in the various examples described above, air is drawn into the security apparatus 100 through an ingress vent 156 wherein the ingress vent 156 is preferably located adjacent the screening zone 112. Also, preferably, air flows from the screening zone 112, through the conduit 106, into the observation room 104 (and in the second observation room 132, if applicable), and out one or more egress vents 158, one of which is preferably located adjacent the observation room 104.

FIG. 4 also shows a preferred configuration in which a first inner barrier 159 and a second inner barrier 160 are included. These inner barriers can include, for example, actual doors or downward-facing blower fans (commonly referred to as "air curtains"). A purpose of the inner barriers is to further insulate the air within the screening zone 112 from air outside the screening station 102 with regard to, for example, temperature, humidity, and/or odors outside the screening station 102. Also, the space between the second inner barrier 160 and the second door 122 allows time for the second door 122 to become locked during a triggering event before the odor emitter(s) in the screening station 102 have had time to pass through the second door 122.

FIG. 5 shows an end view of a security apparatus 161 that includes the screening station 102, the observation room 104, the conduit 106, the airflow inducer 110, the screening zone 112, the animate odor detector 118, the porous structure 124, the engagement apparatus 136 and the sensing device 138; however, the observation room 104 is not situated remote from the screening station 102 and the conduit 106 consists essentially of the porous structure 124.

Figure 6:
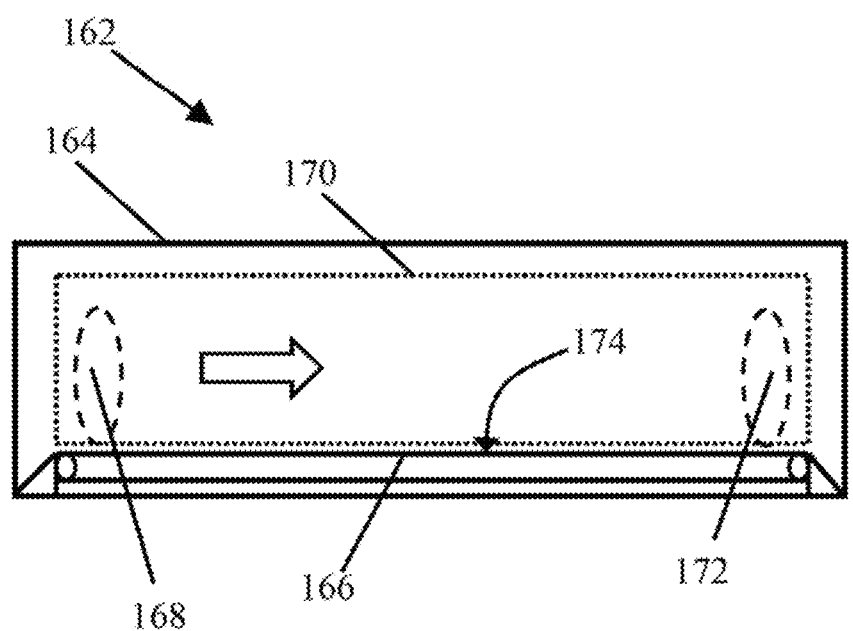
FIG. 6 shows a somewhat schematic side view of a screening station.

FIG. 6 shows part of a security apparatus 162 including a screening station 164 that further includes a conveyor system 166 to convey an odor emitter from a first location 168 within a screening zone 170 to a second location 172 within the screening zone 170. The conveyor system 166 further includes a conveyor support surface 174 for supporting an odor emitter during a screening period. The duration of the screening period generally depends on the speed of the conveyance system because odor emitters preferably remain stationary relative to the conveyor support surface 174 during the screening period. By providing the conveyance system 166, the movement of multiple odor emitters through the screening zone 170 is standardized to better ensure quality screening results by presenting a similar test sample to the animate odor detector 118 for each odor emitter. The conveyance system 166 can be in the form of, for example, one or more conveyor belts propelled by a motor or an escalator including a plurality of steps.

Figure 7:
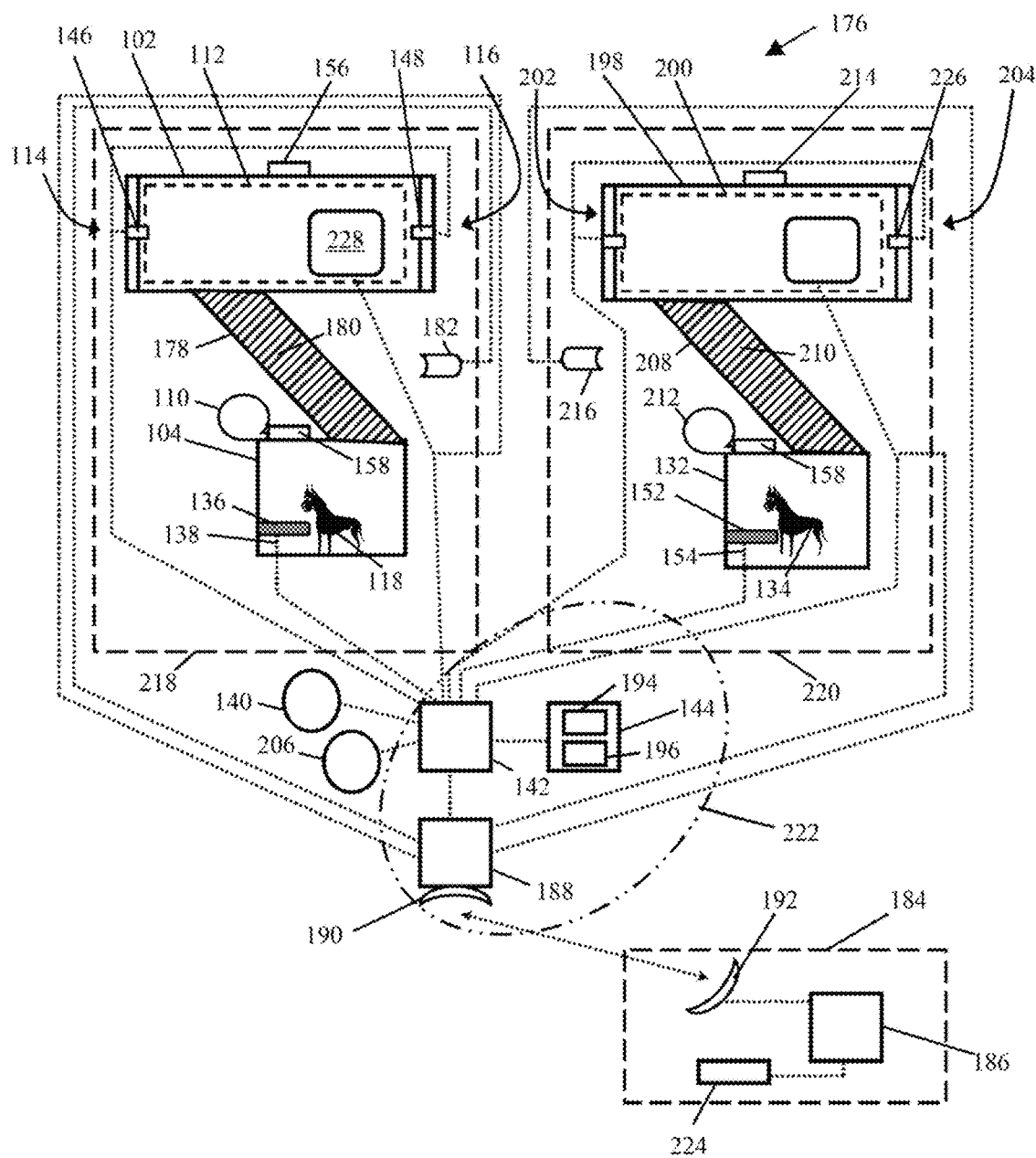
FIG. 7 shows a somewhat schematic side view of a target odor detection apparatus.

FIG. 7 shows a security apparatus 176 including the screening station 102, the observation room 104, the airflow inducer 110, the screening zone 112, the ingress portal 114, the egress portal 116, and the animate odor detector 118 located in the observation room 104. The security apparatus 176 further includes a first enclosed passageway 178 defining a first transfer zone 180 between the screening zone 112 and the observation room 104, wherein the first enclosed passageway 178 is attached adjacent the screening station 102 and adjacent the observation room 104 to provide a passageway for gas to flow from the screening zone 112, through the transfer zone 180, to the observation room 104. The security apparatus 176 also includes a first camera 182 for acquiring a first set of visual data from a first area of interest in or adjacent the security apparatus 176. The security apparatus 176 also includes a remote supervision zone 184 including an electronic display apparatus 186 for a person to remotely monitor the first area of interest. A relay system 188 is also preferably provided to relay visual data from the first camera 182 to the electronic display apparatus 186. Preferably, the relay system 188 includes a first visual data transmitter 190 and a first visual data receiver 192.

In one embodiment, visual data (e.g., video or time lapse photography) is recorded in temporary memory storage 194 (e.g., volatile memory such as, for example, random access memory (RAM) of various forms) and such visual data is maintained for a limited period of time (e.g., one hour) before it is deleted or otherwise overwritten by more current visual data. If a triggering event occurs, in response to a signal from the sensing device 138, the computational device 142 begins recording visual data on permanent memory storage 196 (e.g., non-volatile memory of various forms including read only memory (ROM) of various forms) and retrieves some or all of the visual data stored on temporary memory storage 194 and saves that visual data to permanent memory 196. Additionally or alternatively, if a triggering event occurs, in response to a signal from the sensing device 138, the computational device 142 flags the visual data recorded proximate that time period with a time stamp.

FIG. 7 also shows a second screening station 198 including a second screening zone 200 defined between a second ingress portal 202 and a second egress portal 204. The second observation room 132, including the second engagement apparatus 152 and the second sensing device 154 attached adjacent thereto, is also shown. The second sensing device 154 is in communication with a second event indicator 206 and the computational device 142, which further includes the internal or external memory unit 144. Data corresponding to a minimum threshold of input on the second engagement apparatus 152 (e.g., a minimum pressure value, a minimum number of scratches value, a minimum vibration value) is saved, uploaded, downloaded, or otherwise provided to the memory unit 144. During operation of the security apparatus 176, the second engagement apparatus 152 is substantially continuously monitored by the computational device 142 so that the second event indicator 206 is activated if/when an animate odor detector engages the second engagement apparatus 152 with at least a minimum threshold of input force and/or activity. A second enclosed passageway 208 defines a second transfer zone 210, wherein the second enclosed passageway 208 is attached adjacent the second screening station 198 and the second observation room 132 to provide a passageway for gas to flow from the second screening zone 200, through the second transfer zone 210, to the second observation room 132. The second animate odor detector 134 is located in the second observation room 132, and a second air inducer 212 is provided for inducing air flow from within the second screening zone 200, through the second transfer zone 210, and to the second observation room 132 to entrain odors in the second observation room 132 that were emitted in the second screening zone 200 so that the second animate odor detector 134 is exposed to the entrained odors to screen the odors for one or more target odors. A second ingress vent 214 is preferably included to selectively draw ambient air into the screening zone as needed.

Preferably, the security apparatus 176 further includes a second camera 216 for acquiring a second set of visual data from a second area of interest. In one embodiment, the first area of interest is located in a first geographic area 218 including the first screening station 102 and the first observation room 104, and the second area of interest is located in a second geographic area 220 including the second screening station 198 and the second observation room 132. In this embodiment, the relay system 188 relays the second visual data from the second camera 216 to the electronic display apparatus 186, and a person can remotely monitor the first area of interest and the second area of interest at the remote supervision zone 184. The first geographic area 218 can be, for example, at least 50 feet from the second geographic area 220. In other embodiments, the first geographic areas 218 can range from about 1000 ft to about 5500 ft from the second geographic area 220. In other embodiments, the first geographic area 218 is at least 100 miles from the second geographic area 220, and these areas can be separated by thousands of miles if necessary. In other embodiments, the first geographic area 218 is a distance of at least about 5000 feet from the second geographic area 220 and the remote supervision zone 184, and the second geographic area 220 is a distance of at least about 5000 feet from the remote supervision zone 184. These distances are made possible by modern wired and/or wireless communications technologies including, without limitation, cellular communications, satellite communications, Wi-Fi™ or other IEEE 802.11 standard based technology, Bluetooth™ technology, and other electromagnetic communication technologies whether digital or analog.

With regards to the security apparatus 176 described above, the first enclosed passageway 178 and the second enclosed passageway 208 can be elongate conduits, providing for increased distance between the respective screening stations and observation rooms. Alternatively or additionally, the first enclosed passageway 178 and the second enclosed passageway 208 can include, for example, porous structures like the porous structure 124 defined above with regards to the security apparatus 100 in FIG. 5.

The security apparatus 176 can further include a control system 222 in communication with the first sensing device 138 and a manual input apparatus 224 located in the remote supervision zone 184. The manual input apparatus 224 is for selective activation by a person in response to observing an event of interest displayed on the electronic display apparatus 186, whereby activation of the manual input apparatus 224 and/or triggering of the first sensing device 138 causes the control system 222 to generate a control signal directed to a security asset 226 to activate the security asset 226. In embodiments including the second sensing device 154, the control system 222 is in communication with the first sensing device 138, the second sensing device 154, and the manual input apparatus 224. A security asset 226 can include, for example, a door, a door lock, an air inducer, a siren, a light, a fire suppression system (e.g., sprinkler system), a repulsing agent emitter (e.g., pepper spray nozzle), and/or a specially trained person contacted via telecommunication equipment (e.g., a text message or an e-mail message indicating an event of interest has occurred at a specified location).

In related embodiments, the security apparatuses 176 described above can further include an electronic scanning apparatus 228 located within or adjacent the screening station 102. By including the scanning apparatus 228, an odor emitter passing through the screening zone 112 can be screened by the animate odor detector 118 for target odors and also screened by a person monitoring the electronic scanning apparatus 228. The electronic scanning apparatus 228 can include, for example, a metal detector and/or a body image scanner as used in many airports. In a preferred embodiment, the electronic scanning apparatus 228 is in communication with the relay system 188 and/or the control system 222 so that events that trigger the electronic scanning apparatus 228 observed by a person in the remote supervision zone 184 or otherwise made to generate a control signal directed to one or more security assets 226 to activate the security asset 226.

Figure 8A:
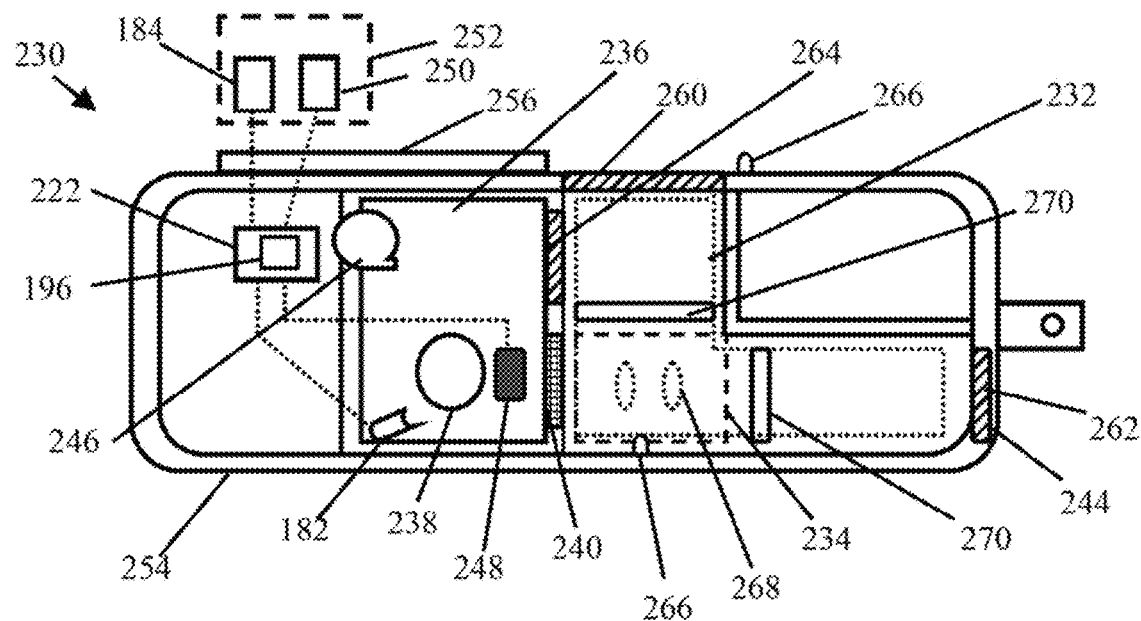
FIG. 8A shows a somewhat schematic top view of a mobile target odor detection apparatus.
Figure 8B:
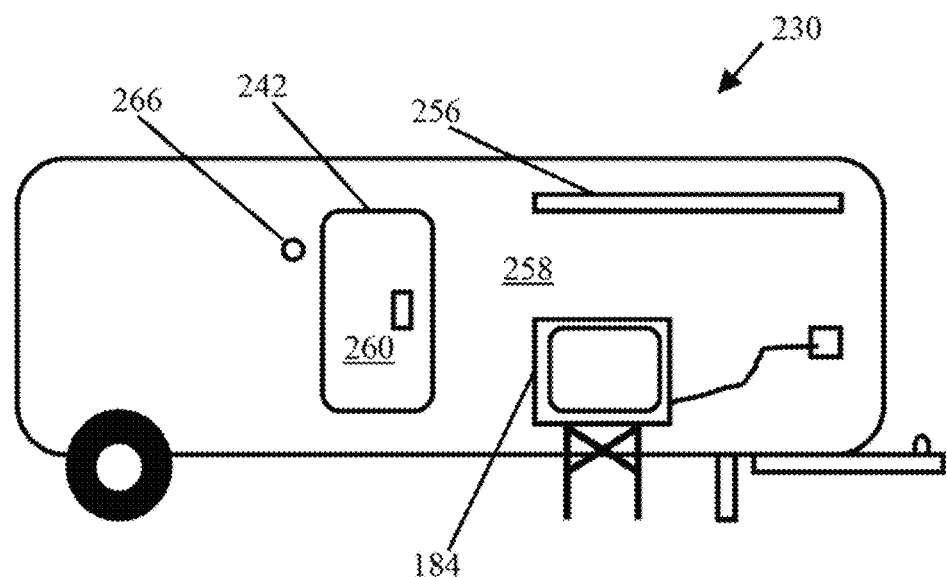
FIG. 8B shows a somewhat schematic side view of the mobile target odor detection apparatus shown in FIG. 8A.

FIGS. 8A and 8B show a mobile version of a security apparatus 230 including a screening chamber 232; a screening zone 234 within the screening chamber 232; an observation chamber 236 for situating an animate odor detector 238 to screen odor emitters for target odors as the odor emitters pass through the screening zone 234; a porous structure 240 through which air can flow from the screening zone 234 to the observation chamber 236; at least one ingress portal 242 through which an odor emitter can enter into the screening chamber 232; preferably, an egress portal 244 through which an odor emitter exits from the security apparatus 230; an air flow inducer 246 for inducing air flow from within the screening zone 234, through the porous structure 240, and into the observation chamber 236 to be screened by the animate odor detector trained to detect a target odor and perform a trained signal when detecting a target odor; and a sensing device 248 in communication with an event indicator 250. The animate odor detector 238 is trained to engage the sensing device 248 if the animate odor detector 238 senses a target odor wherein a pre-set amount of engagement of the sensing device 248 triggers the sensing device 248, which, in turn, triggers the event indicator 250 to indicate that a target odor has been detected. Other features described above regarding other non-mobile embodiments of security devices can be incorporated into the mobile security apparatus 230 such as, for example, the control system 222 shown in FIG. 7. The mobile security apparatus 230 is preferably housed within a trailer, but other embodiments are contemplated such as, for example, a bus, an RV, a van or other similarly sized mobile vehicle.

Preferably, the mobile security apparatus 230 also includes a supervision zone 252 (which optionally can be remote from the screening chamber 232 as described with respect to other embodiments above), a first camera 182, and an electronic display apparatus 184. If the supervision zone 252 is located directly outside a vehicle structure 254, a retractable awning 256 is preferably attached adjacent an outside surface 258 of the vehicle structure 254 to provide some protection from the elements. Preferably, a first door 260 is included to cover the ingress portal 242 and, if applicable, a second door 262 is preferably provided to cover the egress portal 242. In embodiments in which access to the observation chamber 236 is made through the ingress portal, an access door 264 is preferably provided to separate the screening chamber 232 from the observation chamber 236. In one embodiment, the security apparatus 230 includes one or more queue indicators 266 such as, for example, lights that shine green when it is time for an odor emitter to advance and that shine red when it is time for an odor emitter to stand still. Additionally or alternatively, one or more queue indicators may include an automated voice system that gives audible commands through a speaker system, wherein different commands in different languages can be stored in a memory module such as, for example, permanent memory storage 196. These and related features are also used in other non-mobile embodiments described herein and, preferably, the violation of a queue indicator results in a triggering event.

In one embodiment, a pair of foot pads 268 (e.g., foot shaped decals) can be provided to show an odor emitter how and where to stand in the screening zone 234. To better ensure that an odor emitter is standing in the proper position, the foot pads 268 may further include one or more sensors (e.g., a piezoelectric pressure pad, an accelerometer, or other sensor like those used with respect to the engagement apparatuses described herein) to detect whether an odor emitter is stepping on the foot pads 268 properly. These and related features are also used in other non-mobile embodiments described herein and, in some embodiments, detection of an improper stance results in, for example, a local alarm to notify local security personnel to assist an odor emitter through the applicable screening zone. Alternatively, intentional improper standing as evidenced, for example, by camera footage, can result in an automatic or manual triggering event.

In some embodiments, the screening zone 234 is further isolated by barriers 270 (e.g., flexible polymeric curtains or small doors) to further reduce the volume of air in the screening zone 234.

Figure 9A:
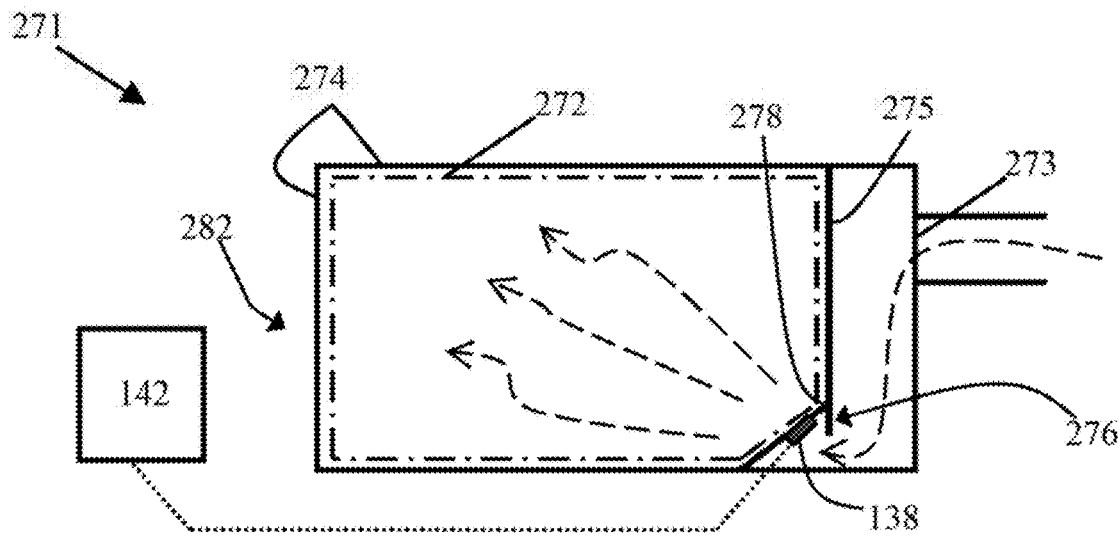
FIG. 9A shows a somewhat schematic side view of an animate odor emitter enclosure apparatus.
Figure 9B:
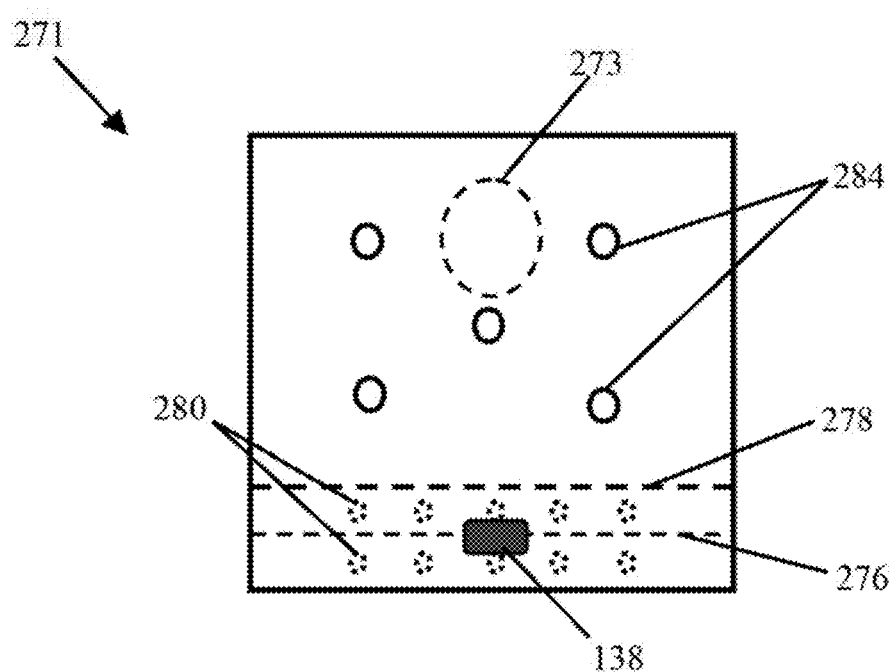
FIG. 9B shows a somewhat schematic end view of the animate odor emitter enclosure apparatus shown in FIG. 9A.

FIGS. 9A and 9B show an embodiment of an animate odor detector enclosure 271 for enclosing an animate odor detector in an observation zone 272, creating positive pressure within the enclosure 271, and for better ensuring that air flowing from a screening zone and through an air inlet 273 is encountered by an animate odor detector within the enclosure 271. The dotted arrows in FIG. 9A show a general pattern of airflow that forces air to an area where, for example, a dog would typically sniff (i.e., near the ground). The enclosure 271 includes a plurality of substantially nonporous walls 274 and an air baffle 275 to preferably redirect incoming air to a bottom portion 276 of the air baffle 275. The air baffle 275 preferably further includes an angled engagement member 278. In preferred embodiments, the angled engagement member 278 includes one or more ingress apertures 280 through which air flows from a screening zone. The angled engagement member 278 can form a portion or all of the engagement apparatus 136 (or the second engagement apparatus 152) described above. The enclosure 271 preferably further includes the sensing apparatus 138 (or the sensing apparatus 154) for relaying engagement activity to, for example, the computational device 142 when or soon after an animate odor detector engages the angled engagement member 278 by, for example, scratching, pouncing, touching, or other engagement activity with the angled engagement member 278. An egress portion 282 includes one or more egress apertures 284 through which air moves out of the enclosure 271, and the total air flux area of the one or more egress apertures 284 is preferably less than the total air flux area of the one or more ingress apertures 280 to help create a positive pressure within the enclosure 271. Also, the relative positioning of the one or more ingress apertures 280 with respect to the relative positioning of the one or more egress apertures 284 better ensures that air must pass by the animate odor emitter, thereby increasing the opportunity for the animate odor detector to detect a target odor if such odor is present in the air flowing through the enclosure 271. The enclosure 271 is preferably made of clear Polymethyl methacrylate (PMMA) or other substantially transparent thermoplastic such as, for example, polycarbonate (PC).

Figure 11:
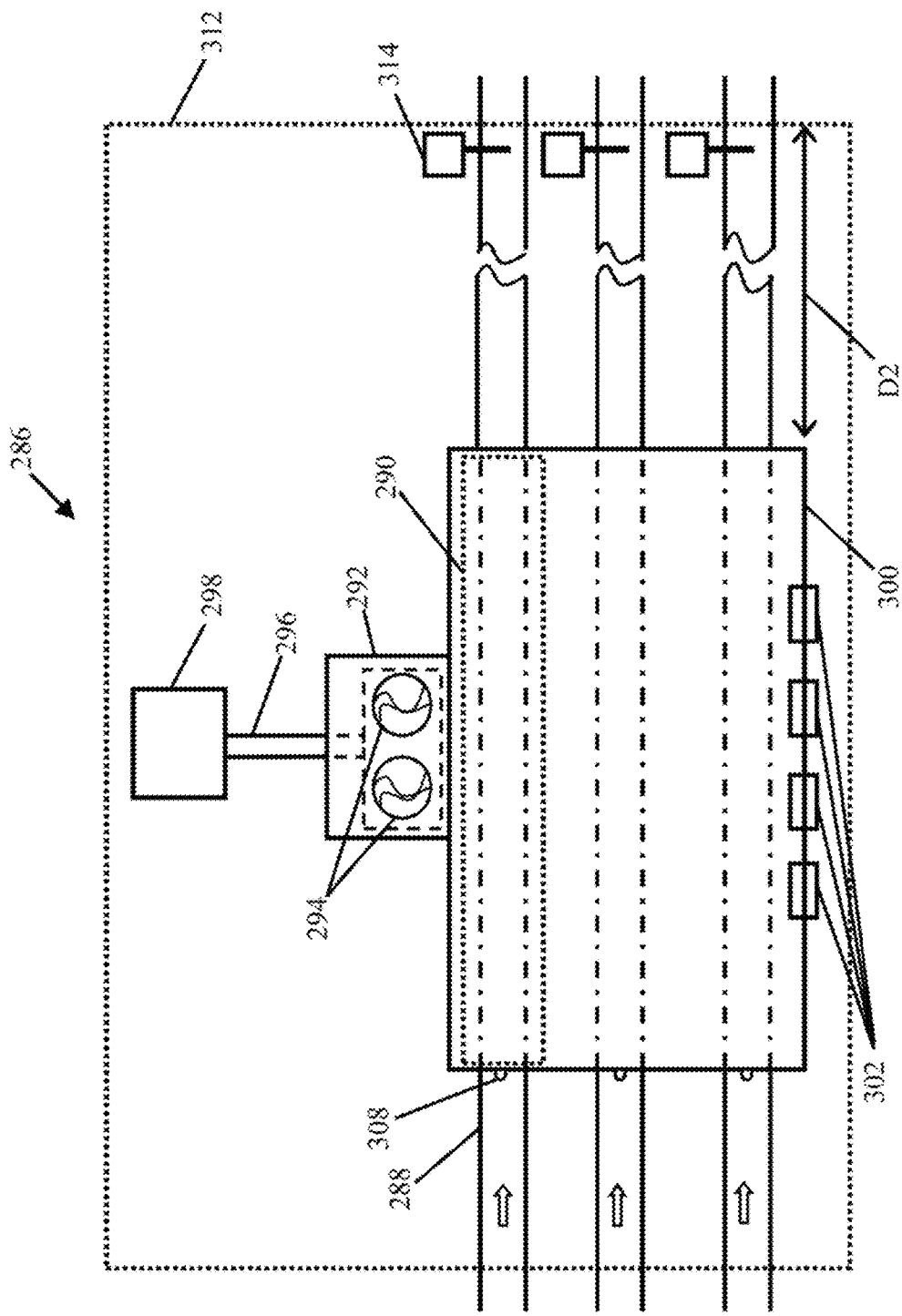
FIG. 11 shows a somewhat schematic top view of the target odor detection apparatus shown in FIG. 10.

FIGS. 10 and 11 show a security apparatus 286 for screening multiple conveyances (e.g., cars, trucks, tractors, motorcycles). The security apparatus 286 includes at least one lane 288 for a conveyance to pass over, a substantially enclosed passageway 290 through which the at least one lane 288 extends, a primary exhaust chamber 292, an air mixer 294 (e.g., mechanical fan) for creating turbulent air conditions within the primary exhaust chamber 292, a duct 296 for directing a fraction of the total airflow in the primary exhaust chamber 292 to an observation room 298 similar or identical to the observation rooms (104, 132) described above with respect FIGS. 1, 3, and 7. The fraction of total airflow directed through the duct 296 preferably ranges from about 5% to about 15%, and more preferably about 10%, by volume of the total airflow flowing through the primary exhaust chamber 292. The passageway 290 further includes a lateral portion 300 including a plurality of air inducers 302 for directing air within the passageway 290 to the primary exhaust chamber 292; an entrance aperture 304 through which conveyances can enter the passageway 290; and an exit aperture 306 through which conveyances can exit the passageway 290.

Preferably, the flow of traffic along each lane is controlled by one or more queue indicators 308 (e.g., a traffic light). Preferably, a maximum speed limit for conveyances is posted and monitored for each conveyance as each conveyance passes through the passageway 290. Such speeds are preferably monitored using, for example, radar or laser detection devices 310 commonly used by traffic law enforcement personnel. A security zone 312 is defined and controlled up to a defined distance D2 from the exit aperture 306 so that if an animate odor detector in the observation room 298 exhibits a trained response, security personnel and/or automated control system(s) have adequate time to stop traffic within the security zone 312 to more closely inspect the one or more conveyances that were passing through the passageway 290 near the time when the animate odor detector exhibited a trained response. This can be accomplished at least in part, for example, by one or more security barriers 314. The defined distance D2 preferably ranges from about one quarter mile to about one mile and, more preferably, from about one half mile to about three-quarters of a mile.

By creating turbulent air conditions in the primary exhaust chamber 292, the air therein quickly becomes well-mixed such that a sample of the air within the primary exhaust chamber 292 is a more reliable cross-sectional sample of the entire air environment within the passageway 290. Thus, when air from the duct 296 is exposed to an animate odor detector, the animate odor detector is more likely to detect any target odor that may be (or very recently was) present within the covered passageway 290.

Figure 12:
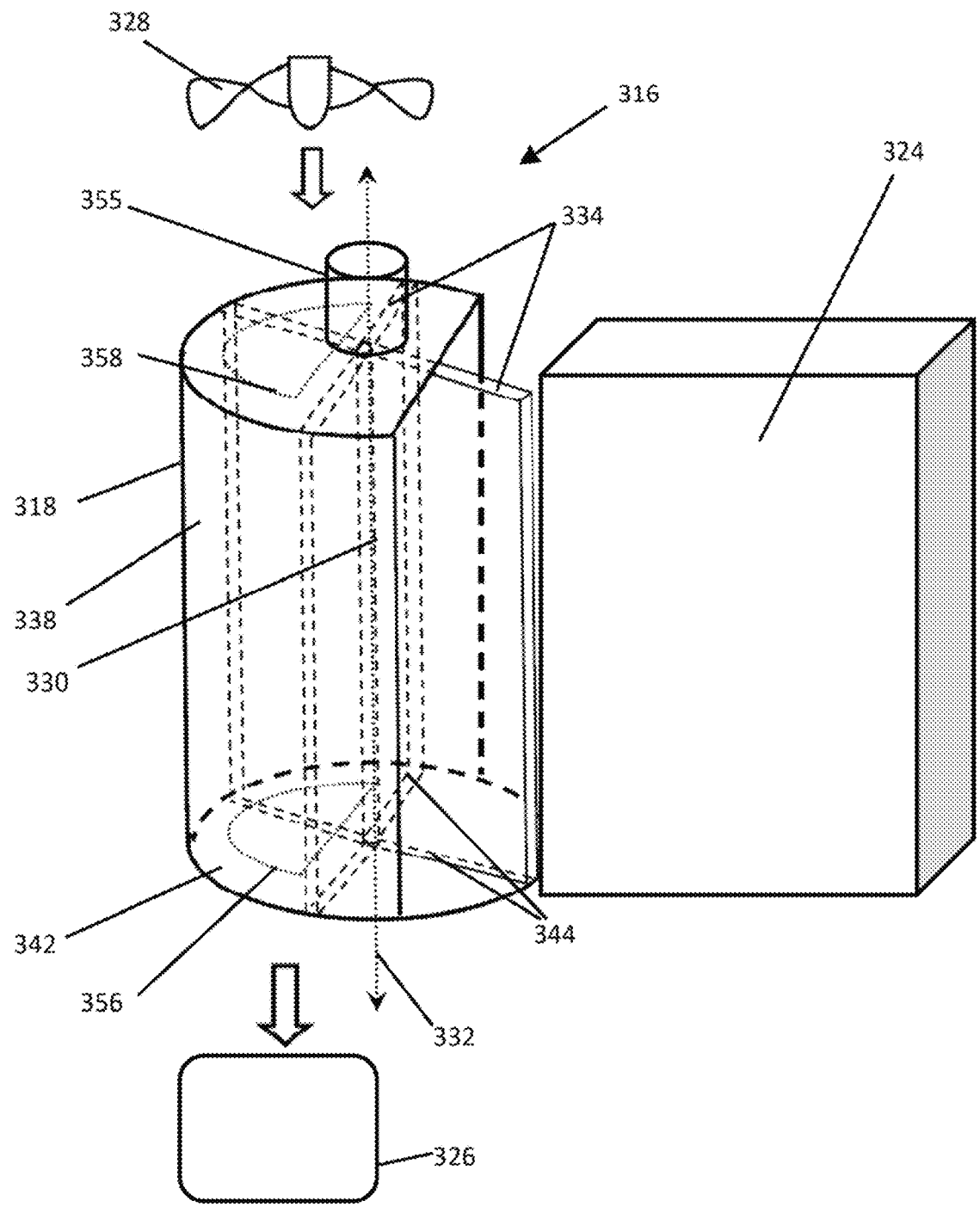
FIG. 12 shows a schematic and perspective view of a target odor detection apparatus that includes a rotatable door assembly.
Figure 13:
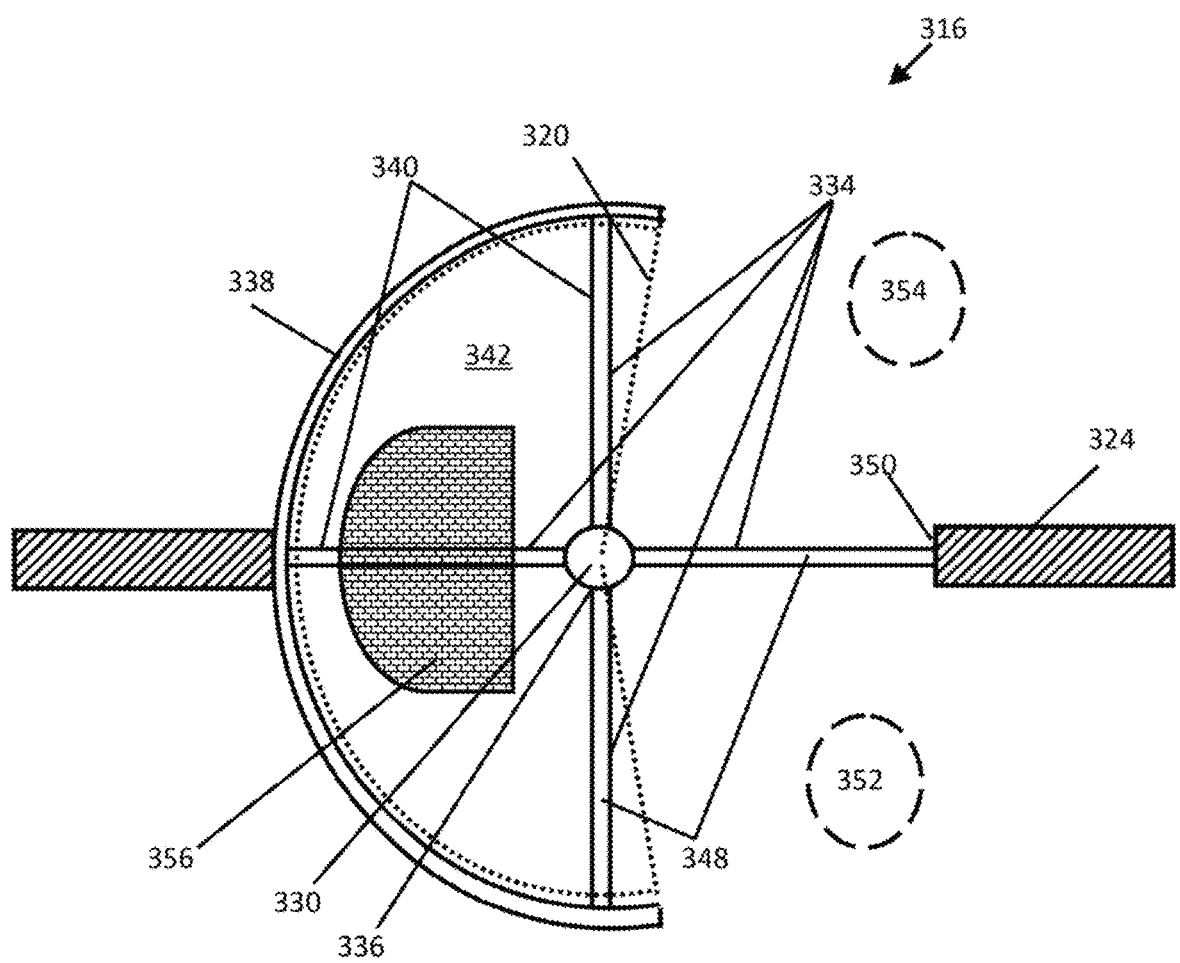
FIG. 13 shows a schematic plan view from top down of the target odor detection apparatus shown in FIG. 12.

FIGS. 12-13 show somewhat schematic views of a screening apparatus 316 including a rotatable door assembly 318 defining a screening zone 320, a barrier 324, an observation room 326, and an airflow inducer 328. The rotatable door assembly 318 includes a vertical member 330 that is oriented along a centrally-located vertical axis 332 and a plurality of panels 334 extending outward from the vertical member 330 forming a rotatable door 336. The rotatable door assembly 318 also includes a curved wall 338 adjacent which the respective outward edges 340 of the panels slide past during a full rotation of the rotatable door 336; a base member 342 over which the respective bottom edges 344 of the panels slide past during a full rotation of the rotatable door 336; and a ceiling member 346 under which the respective top edges 348 of the panels slide past during a full rotation of the rotatable door 336. The screening zone 320 is generally defined as the three-dimensional space between the curbed wall 338, the vertical member 330, the base member 342, and the ceiling member 346. The barrier 324 includes a barrier edge 350 which the respective outward edges 340 of the panels slide past during a full rotation of the rotatable door 336. The barrier 324 helps separate an entrance zone 352 from an exit zone 354. The barrier 324 might include, for example, the wall of a building wherein the exit zone 354 includes, for example, the interior lobby of the building.

The example shown in FIGS. 12-13 includes an electric motor 355 that can be used to rotate the rotatable door 336. Although the motor 355 is provided as example, it is understood that a motor is not necessary as many rotatable doors operate by manual pushing of a person moving through a rotatable door assembly. Furthermore, any device disclosed herein requiring a power source (e.g., electricity) to operate should be understood to receive such power from proximate electrical power outlets, mobile gasoline or other generator device, or one or more batteries.

Figure 14:
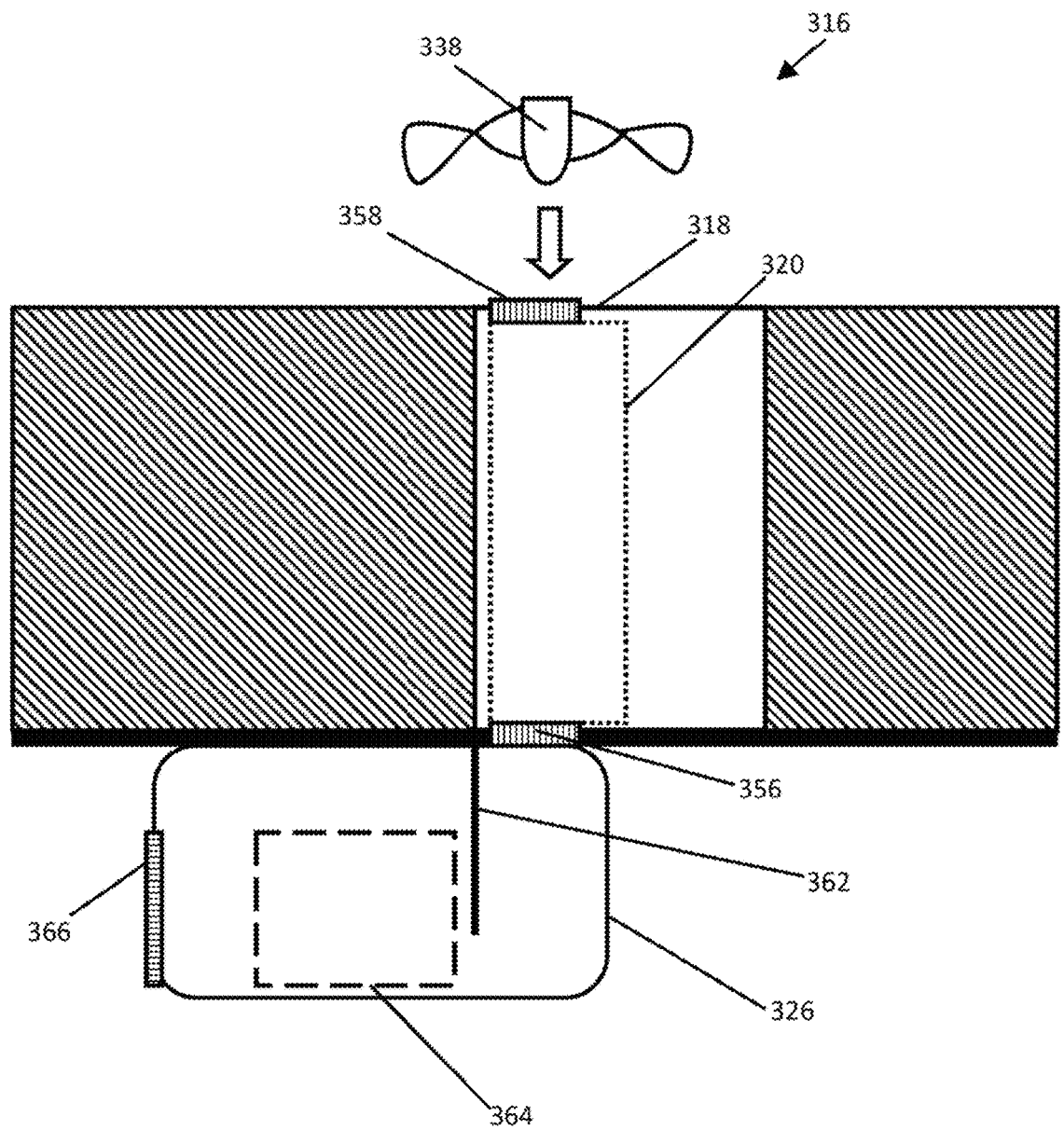
FIG. 14 shows a schematic side view of the target odor detection apparatus shown in FIG. 12.
Figure 15:
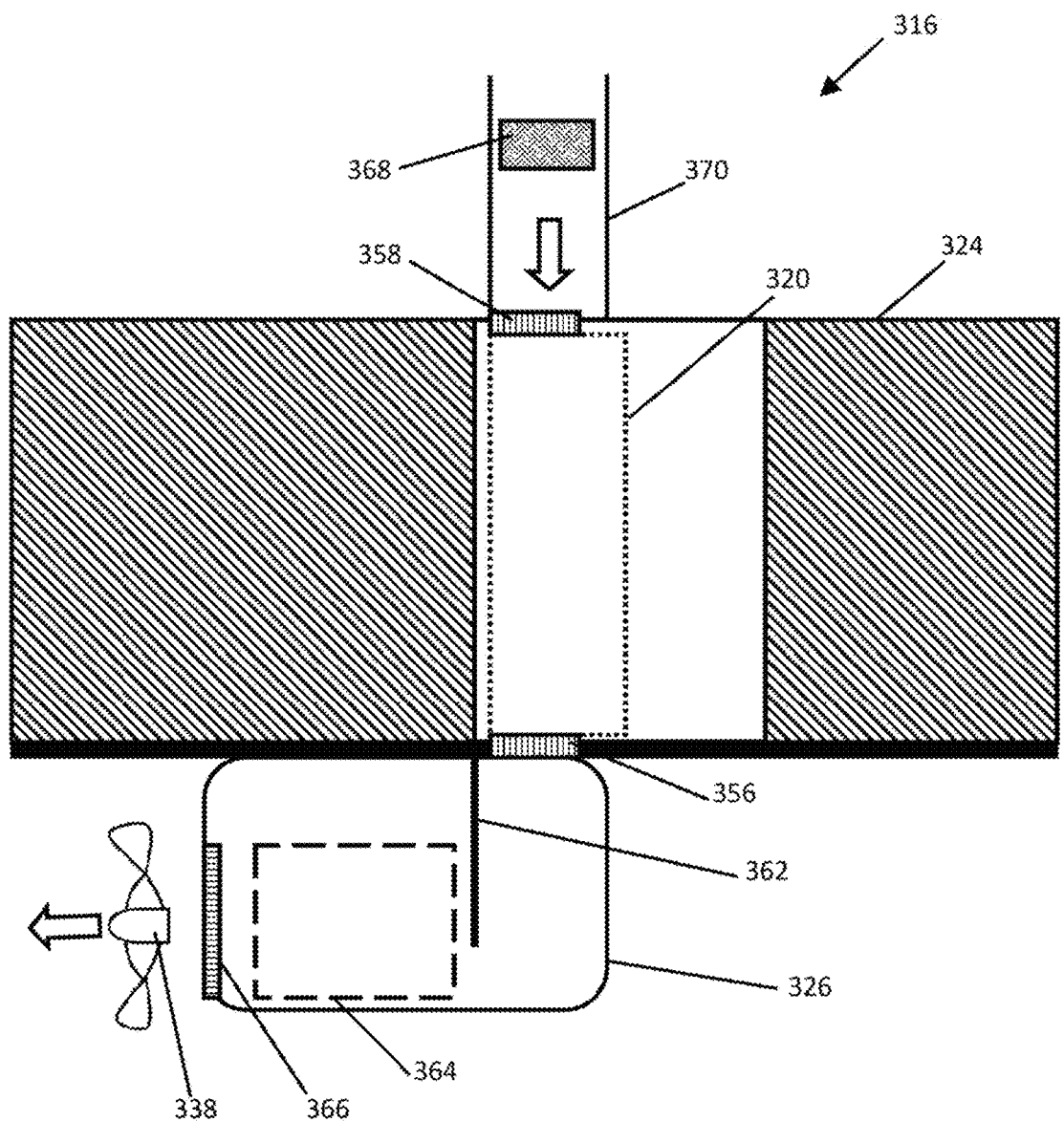
FIG. 15 shows a schematic side view of a target odor detection apparatus that includes a rotatable door assembly.
Figure 16:
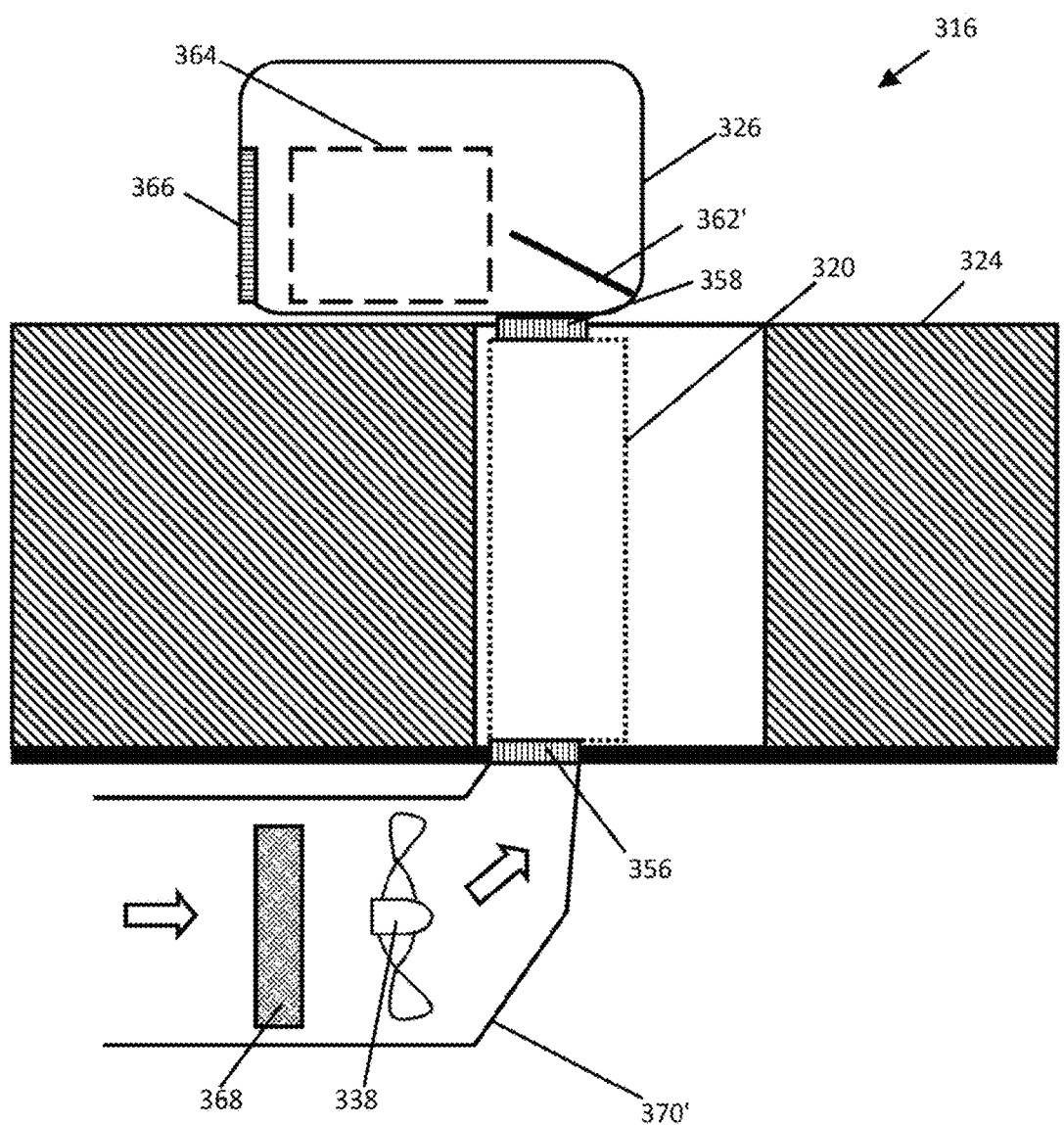
FIG. 16 shows a schematic side view of another target odor detection apparatus that includes a rotatable door assembly.
Figure 17:
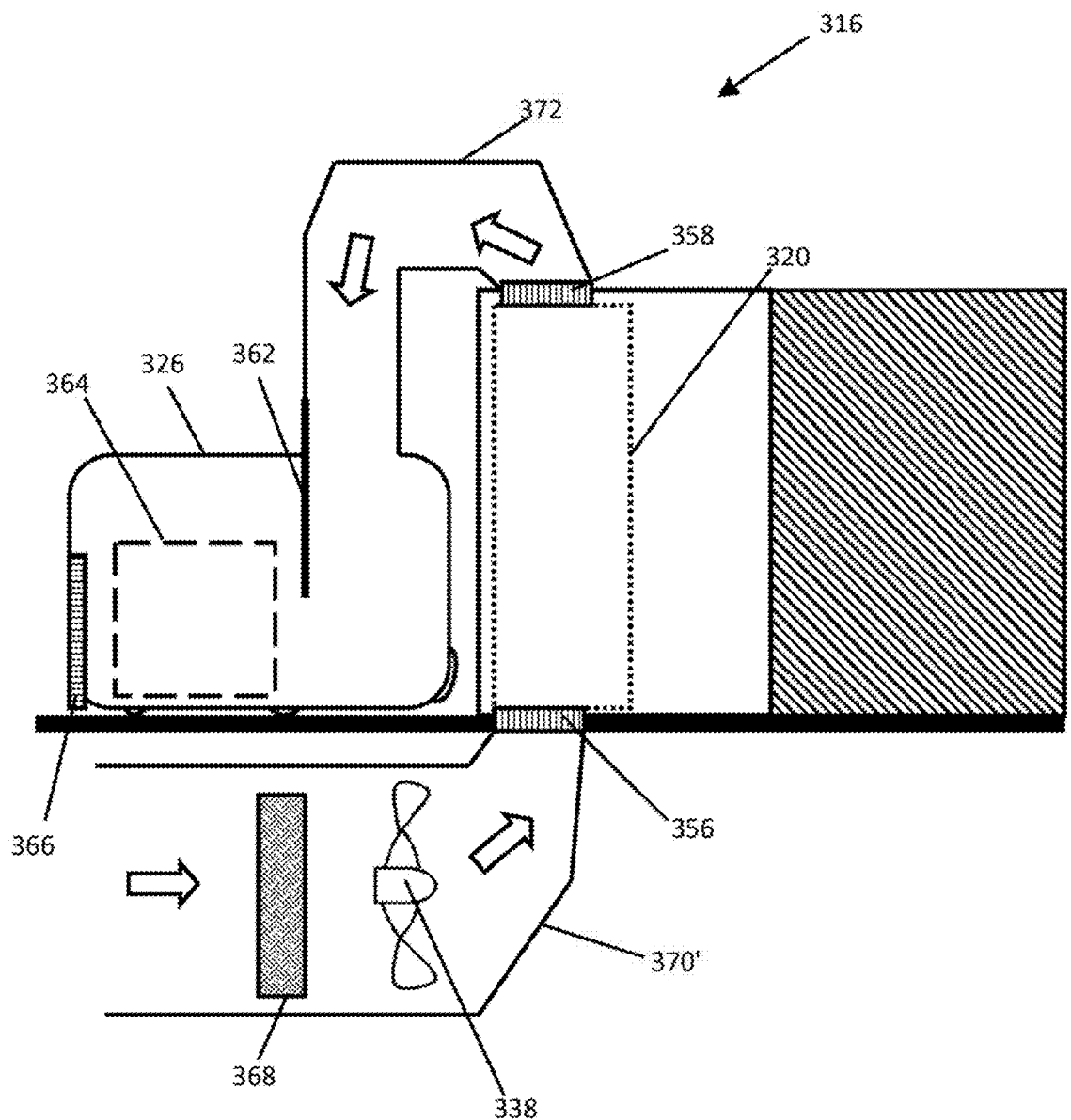
FIG. 17 shows a schematic side view of yet another target odor detection apparatus that includes a rotatable door assembly.

The base member 342 includes a base vent 356 through which air can flow and, likewise, the ceiling member 346 includes a ceiling vent 358 through which air can flow. In one embodiment, the airflow inducer 328 includes a fan and, depending on the position of the fan, can either blow air through the screening zone 320 or draw air through the screening zone 320. The example shown in FIG. 14 shows air being blown through the screening zone 320, through the base vent 356, past an air baffle 362, through an animate odor detector enclosure 364, and then through an exit vent 366. FIG. 15 shows an example in which the airflow inducer 328 draws air through the screening zone 320. A filter 368 is preferably included to filter air in an entrance conduit 370 before the air passes through the screening zone 320, thereby removing any contaminants that might alter the sample of air taken from the screening zone 320 to the observation room 326. FIG. 16 shows a related schematic diagram showing the observation room 326 located above the screening zone 320 and a different variation of an entrance conduit 370' and an air baffle 362'. FIG. 17 shows an example in which the observation room 326 is at substantially the same elevation as the screening zone 320 wherein a transfer conduit 372 is used to channel air from the ceiling vent 358 to the observation room 326.

Figure 18:
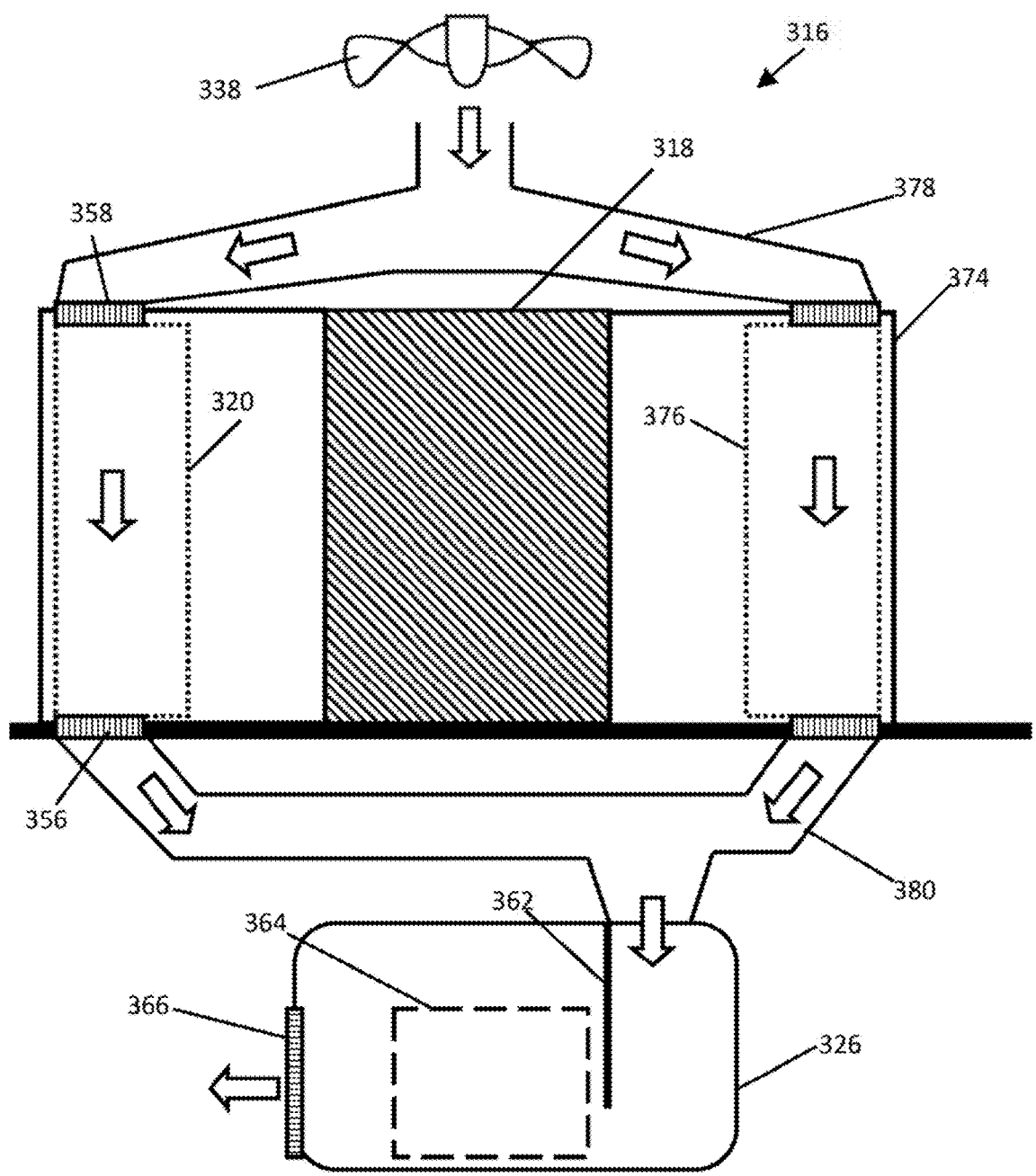
FIG. 18 shows a schematic side view of a target odor detection apparatus that includes two rotatable door assemblies.

FIG. 18 shows an example of the screening apparatus 316 that includes a second rotatable door assembly 374 so that multiple odor emitters can be screened at the same time, thereby increasing the rate, for example, at which persons can enter a secured building. In this example, air from the screening zone 320 and a second screening zone 376 in the second rotatable door assembly 374 is channeled to the observation room 326 for screening. Air is brought into the respective screening zones via an entrance conduit 378 and is channeled to the observation room 326 from the respective screening zones via an exit conduit 380.

Figure 19:
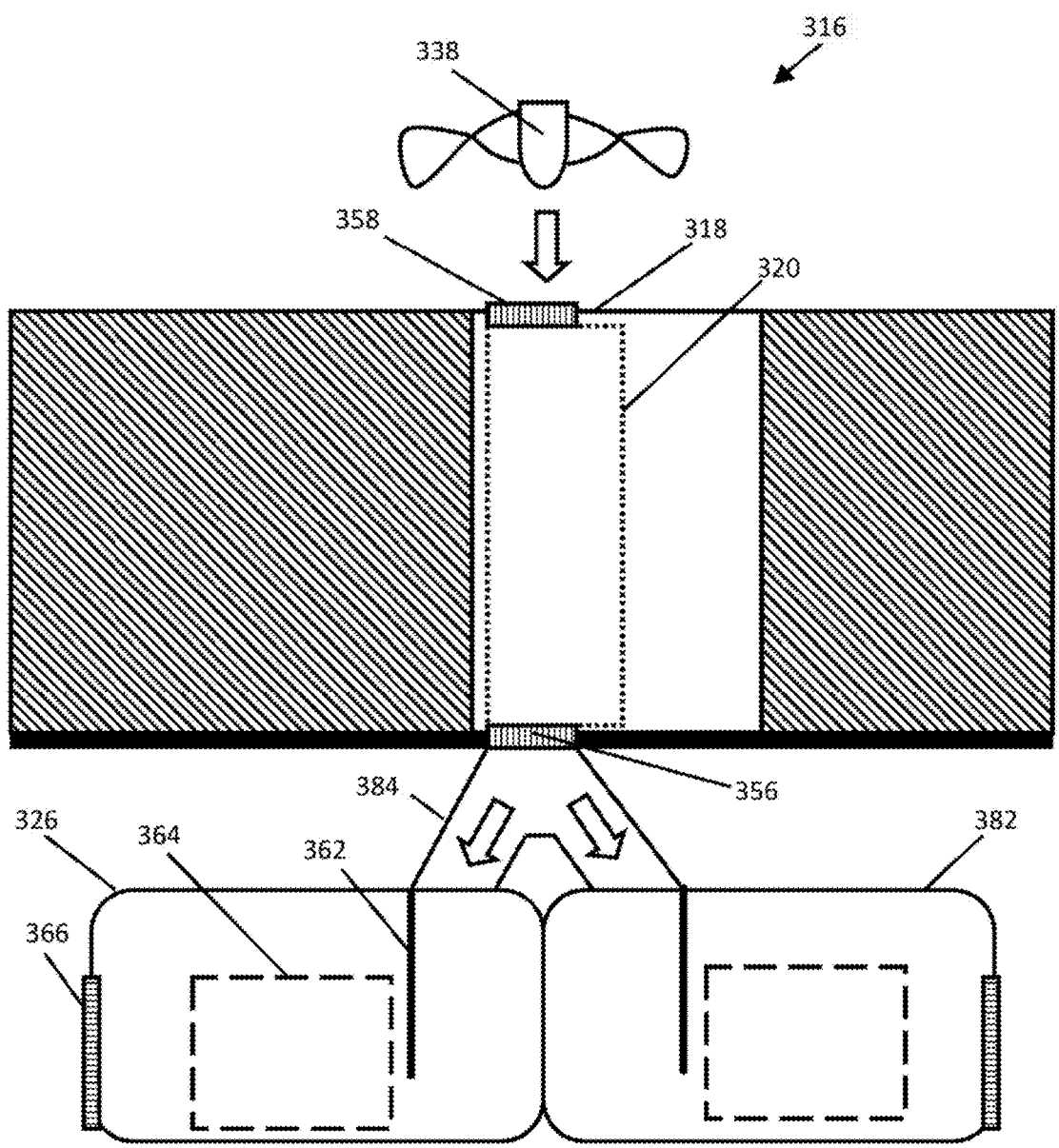
FIG. 19 shows a schematic side view of a target odor detection apparatus that includes a rotatable door assembly and two observation rooms.

FIG. 19 shows an example of the screening apparatus 316 that includes a second observation room 382 for holding a second animate odor detector. Air flows through the screening zone 320 and is channeled through an exit conduit 384 to the respective observation rooms. Preferably, when the first animate odor detector 118 is located in the first observation room 326 and the second animate odor detector 134 is located in the second observation room 382, the animate odor detectors are tasked with screening for different target odors.

Figure 20A:
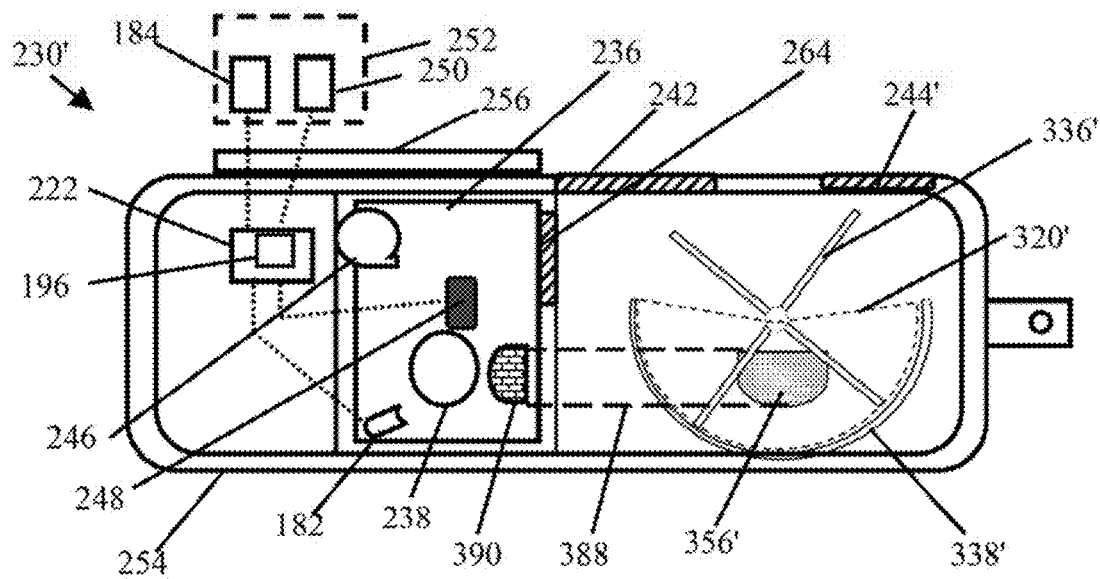
FIG. 20A shows a schematic plan view from the top down of a target odor detection apparatus including a mobile unit and a rotatable door assembly.
Figure 20B:
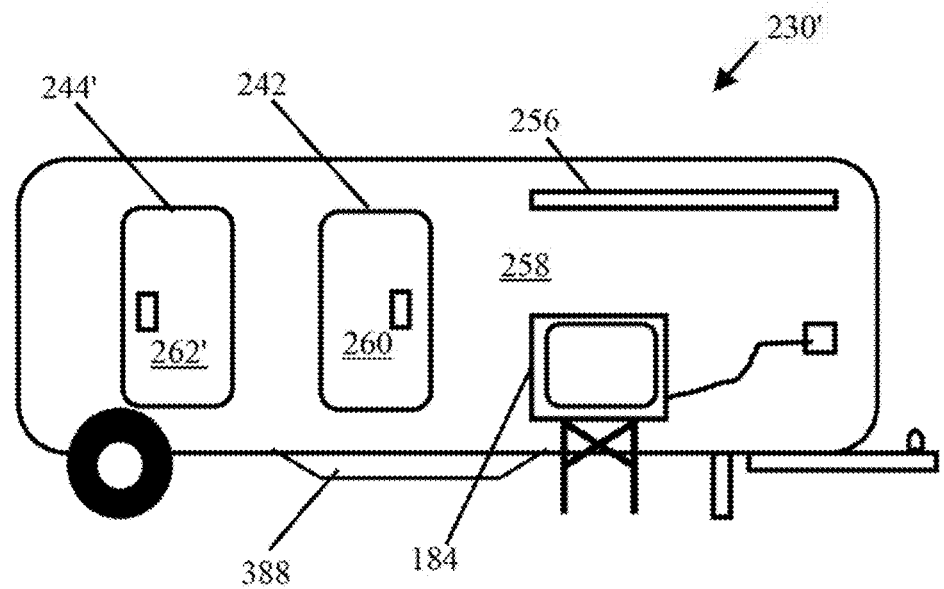
FIG. 20B shows a schematic side view of the target odor detection apparatus shown in FIG. 20A.

FIGS. 20A and 20B show another example of a mobile security apparatus 230' including a rotatable door assembly 386 including a curved wall 338' and rotatable door 336'. A screening chamber 320' is defined therein and a base vent 356' is provided wherein air is moved through the screening zone 320', through the base vent 356', through a base conduit 388, and up through an observation vent 390 located in the observation room 236. An egress portal 244' is shown and an egress door 262' is preferably included. Features of other examples of screening apparatuses not shown in FIGS. 20A-20B are contemplated to be incorporated into the mobile security apparatus 230' such as, for example, a filter, ceiling vent, push or pull (blow or draw) air movement capability, as well as different placement of the base conduit 388. For example, air could be moved upward and over into the observation room in the mobile security apparatus 230' as shown, for example, in FIG. 17.

Other examples of screening apparatuses and security apparatuses as described herein that include rotatable door assemblies are contemplated, and the features of the examples described herein that did not necessarily show use of rotatable door assemblies are further contemplated for use with embodiments that are shown as using rotatable door assemblies.

Various embodiments disclosed herein can be used in many different security situations and applications including, for example, airport security, building security, event security (e.g., a large outdoor concert, a collegiate or professional sporting event), and government structure security. One object of the disclosure is to provide a security apparatus useful for screening an odor emitter for target odors using a standardized triggering system (e.g., the engagement apparatus 136 and the sensing device 138). In this manner, a consistent standard is applied to consistently determine whether an animate odor detector is giving a trained signal or not in response to an odor. Previously, animate odor detectors have been observed by people (e.g., trainers), and different trainers would interpret signals from different animate odor detectors in different ways, thereby causing some degree of inconsistency in determining whether a triggering event has occurred. A related embodiment of the disclosure is to provide a mobile version of a security apparatus as described herein for screening odor emitters for target odors using a standardized triggering system.

Another object of the disclosure is to provide an apparatus to provide distance between the screening zone where odor emitters pass through and the observation room where a screening animate odor detector is usually present, potentially with an accompanying trainer. Placing an observation room a minimum distance from a screening zone is important for various reasons including (1) protecting an animate odor detector trained to screen odor emitters for one or more target odors from weapons used in or near the screening zone (e.g., explosives, chemical weapons, and biological weapons); protecting human and animal odor emitters with animal-related allergies from coming into close proximity with the screening animate odor detector; decreasing the chance that human or animal odor emitters will be aware that the screening animate odor detector is screening them; and/or reducing the anxiety of human or animal odor emitters moving through the screening zone who have animal-related phobias.

Yet another object of the disclosure is to provide a security apparatus that can isolate, repulse, or otherwise control an odor emitter that causes a triggering event. If a non-threatening target odor is detected (e.g., illegal narcotics), the suspected odor emitter can be enclosed within a screening station. Alternatively, if a threatening target odor is detected (e.g., high explosives), the suspected odor emitter can be repulsed from the screening station away from the building/event being secured by use of a repulsing agent (e.g., an automated pepper spray nozzle within the screening station). If the screening station is blast resistant, it may be better to isolate an odor emitter suspected of carrying high explosives within the screening station by automatically closing and locking any applicable doors. If a chemical weapon or biological weapon is detected, an embodiment of a security apparatus as described herein can be configured to automatically close all vents, doors, and other openings to the screening station, thereby virtually sealing the screening station so that such weapons cannot be spread outside of the screening station. Various control logic options using the security apparatuses described herein and variations thereof are contemplated in which certain types of triggering events cause certain security assets to be activated in a specified order or manner. The resultant security measures taken in any given scenario will ultimately depend on the programming of the applicable controller (and associated software, firmware, and/or otherwise), the specific configuration and construction of the security apparatus being used, and the number and types of target odors being screened at any one time.

Another object of the disclosure is to provide a highly reliable security apparatus for screening one or more target odors while also screening odor emitters using other technologies including metal detection, body scanning, bio-scanning (e.g., finger-print scans, retinal scans), badge scanners, and other types of security scanning and screening devices.

Another objective of embodiments described herein include the ability to rapidly screen odor emitters for target odors by temporarily trapping a plume of air around each odor emitter and rapidly moving such plume of air to a nearby observation room for screening by an animate odor detector.

The previously described embodiments of the present disclosure have many advantages, including consistency in sensing target odors and interpreting associated trained signals, protection for screening animate odor detectors and odor emitters alike, protection from blasts or flying projectiles, screening for different types of target odors at one time, visual monitoring of multiple screening stations located very far apart from one another and far apart from the remote supervision zone, automated sensor monitoring of multiple screening stations located very far apart from one another and far apart, mobility of certain versions of the security apparatus, flexibility in programming a security apparatus controller based on the particular situation/event/building for which a security apparatus will be used to protect, and other advantages described herein. The ability to rapidly scan conveyances moving at high rates of speed is a significant improvement over scanning conveyances (e.g., cars) one by one at checkpoints where conveyances must each stop in single file fashion for sometimes extended periods of time.

Although the rapid screening techniques described herein with respect to moving conveyances is not necessarily reliable at detecting small quantities (i.e., less than about 10 kilograms) of a contraband substance (e.g., explosives), the objective is to rapidly eliminate someone to move a conveyance proximate to a secured area and, for example, detonate a large amount of explosives. Similarly, detection of small stashes of narcotics crossing over a federal border is not the goal for this specific exemplary technology. Rather, a primary goal is to rapidly and efficiently identify large quantities of narcotics and other illegal substances to disrupt significant shipments of illegal contraband. Thus, for this particular application, detection of small quantities is not nearly as important as detecting large quantities of contraband substances.

Some advantages of embodiments using rotatable door assemblies include the compact size of the overall apparatus, and the ability to trap discrete plumes of air in a screening zone and quickly move such plume to a nearby observation room for rapid screening.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A method for screening an odor emitter, the method comprising the steps of:
   providing access to an entry point to a security zone for an odor emitter wherein the entry point comprises a rotatable door through which an odor emitter must pass through prior to entering the security zone, wherein the rotatable door includes an enclosed portion defining a screening zone, the enclosed portion including a plurality of adjacent rotatable panes, a curved wall fixed relative to the plurality of rotatable panes, a base member, and a ceiling member;
   moving air through the screening zone wherein at least some of the moved air is directed to an observation room;
   screening the air from the screening zone that has been moved to the observation room; and
   determining whether a target odor is present in the moved air present in the observation room.

2. The method of claim 1 further comprising the step of locking down the rotatable door so that the odor emitter being screened is trapped between the adjacent rotatable panes and the curved wall.

3. The method of claim 1 wherein the step of screening the air from the screening zone that has been moved to the observation room further comprises the sub-step of screening such air using an animate odor detector.

4. The method of claim 1 wherein the step of screening the air from the screening zone that has been moved to the observation room further comprises the sub-step of screening such air using an inanimate odor detector.

5. The method of claim 1 further comprising the step of determining the type of target odor present if a target odor is detected in the moved air present in the observation room.

6. The method of claim 5 further comprising the step of repulsing the odor emitter away from the security zone.

7. The method of claim 5 further comprising closing any vents, doors, or other openings to the screening zone, thereby sealing the screening zone so that any potential airborne threat cannot be spread any further from the screening zone to adjacent areas.

* * * * *

UNITED STATES PATENT AND TRADEMARK OFFICE
CERTIFICATE OF CORRECTION

PATENT NO. : 9,835,602 B2
APPLICATION NO. : 14/326852
DATED : December 5, 2017
INVENTOR(S) : Freddie R. Brasfield It is certified that error appears in the above-identified patent and that said Letters Patent is hereby corrected as shown below:

In the Specification

At Column 1, Line 31:
The sentence should include the word "pedestrians" between the word "from" and the word "and/or".

Signed and Sealed this
Fifteenth Day of May, 2018

Andrei Iancu
*Director of the United States Patent and Trademark Office*